(12) United States Patent
Arciuolo

(10) Patent No.: US 12,041,981 B2
(45) Date of Patent: Jul. 23, 2024

(54) DYNAMIC SOCKS AND ASSOCIATED METHODS

(71) Applicant: ROAR Athletic Performance Corp., Milford, CT (US)

(72) Inventor: Matthew J. Arciuolo, Milford, CT (US)

(73) Assignee: Roar Athletic Performance Corp., Milford, CT (US)

( * ) Notice: Subject to any disclaimer, the term of this patent is extended or adjusted under 35 U.S.C. 154(b) by 121 days.

(21) Appl. No.: 17/399,761

(22) Filed: Aug. 11, 2021

(65) Prior Publication Data

US 2022/0047005 A1 Feb. 17, 2022

Related U.S. Application Data

(60) Provisional application No. 63/063,984, filed on Aug. 11, 2020.

(51) Int. Cl.
*A41B 11/00* (2006.01)
*A41B 11/14* (2006.01)
(Continued)

(52) U.S. Cl.
CPC ........ *A41D 13/0015* (2013.01); *A41B 11/003* (2013.01); *A41B 11/14* (2013.01);
(Continued)

(58) Field of Classification Search
CPC ....... A41B 11/003; A41B 11/00; A41B 11/02; A41B 2300/22
(Continued)

(56) References Cited

U.S. PATENT DOCUMENTS 5,263,923 A * 11/1993 Fujimoto ......... A41D 19/01582
602/62
5,640,714 A * 6/1997 Tanaka ................... A41B 11/00
2/22
(Continued)

FOREIGN PATENT DOCUMENTS

FR 3017031 A1 * 8/2015 ........... A61F 13/085
GB 1177530 A * 1/1970
(Continued)

OTHER PUBLICATIONS

English machine translation of FR 3017031 A1. Via Clarivate Analytics. Translation performed on Sep. 22, 2023. (Year: 2015).*
(Continued)

*Primary Examiner* — Jameson D Collier
(74) *Attorney, Agent, or Firm* — McCarter & English, LLP

(57) ABSTRACT

The present disclosure relates to a dynamic sock, pantyhose, athletic pants/leggings or similar clothing, designed to increase propulsion or restrict motion in human gait as would be advantageous in athletic, lifestyle, medical or similar applications. Similarly, the described invention would be advantageous in sedentary applications to restrict joint angle for various pathologies. The exemplary sock includes an integrated propulsion/tension band with increased elastic/compression/tension capability at specific parts of the foot, ankle and lower leg to increase the tension at the dorsiflexion, midstance or plantarflexion phase of the gait cycle or restrict joint excursion in medical applications to thereby increase the rate, amount and force of plantarflexion or dorsiflexion or restrict motion in the sagittal, transverse or horizontal planes.

16 Claims, 14 Drawing Sheets

(51) Int. Cl.
  *A41D 1/08* (2018.01)
  *A41D 13/00* (2006.01)
(52) U.S. Cl.
  CPC ............ *A41D 1/08* (2013.01); *A41B 2300/22* (2013.01); *A41D 2500/10* (2013.01)
(58) Field of Classification Search
  USPC .................................................. 2/239, 240
  See application file for complete search history.

(56) References Cited

U.S. PATENT DOCUMENTS

| | | | | |
|---|---|---|---|---|
| 5,898,948 | A * | 5/1999 | Kelly ..................... | A41B 11/02 2/239 |
| 6,286,151 | B1 * | 9/2001 | Lambertz ............... | A41D 31/14 2/239 |
| 2005/0076421 | A1 | 4/2005 | Littzi | |
| 2006/0130217 | A1 * | 6/2006 | Lambertz ............... | A41B 11/02 2/239 |
| 2009/0013450 | A1 * | 1/2009 | Lambertz ............. | A41B 11/003 602/65 |
| 2009/0165190 | A1 * | 7/2009 | Araki ....................... | D04B 1/02 66/178 A |
| 2009/0276939 | A1 * | 11/2009 | Sho ........................ | D04B 1/26 66/178 A |
| 2011/0314591 | A1 | 12/2011 | Mitsuno et al. | |
| 2012/0100778 | A1 * | 4/2012 | Cho ........................ | A41D 1/06 450/95 |
| 2012/0102625 | A1 * | 5/2012 | Klein ....................... | D04B 1/04 2/239 |
| 2013/0205839 | A1 * | 8/2013 | Fukui ...................... | D04B 1/26 66/185 |
| 2014/0053610 | A1 * | 2/2014 | Fukui ..................... | D04B 1/102 66/178 A |
| 2014/0331387 | A1 * | 11/2014 | Hennings ............. | A41B 11/003 2/239 |
| 2016/0206462 | A1 * | 7/2016 | Iida ........................ | A61F 5/0111 |
| 2016/0338417 | A1 | 11/2016 | Kehler et al. | |
| 2017/0318872 | A1 * | 11/2017 | Sakai ..................... | A61F 5/0111 |
| 2018/0051401 | A1 * | 2/2018 | Giorgini ................... | D04B 1/24 |
| 2018/0368484 | A1 * | 12/2018 | Baravarian ............ | A41B 11/02 |
| 2019/0350270 | A1 | 11/2019 | Collins et al. | |
| 2019/0350273 | A1 * | 11/2019 | Baravarian .......... | A41B 11/003 |
| 2021/0128338 | A1 * | 5/2021 | Unnava .................. | A41D 27/10 |
| 2021/0145079 | A1 * | 5/2021 | De Freitas Silva .. | A41B 11/003 |
| 2022/0322756 | A1 * | 10/2022 | Stull ...................... | A41B 11/02 |

FOREIGN PATENT DOCUMENTS

| | | |
|---|---|---|
| JP | 2006-312789 A | 11/2006 |
| JP | 2014-019994 A | 2/2014 |
| KR | 101875158 B1 | 7/2018 |
| WO | WO-2007147980 A2 * | 12/2007 ........... A41B 11/003 |
| WO | WO 2019/003145 A1 | 1/2019 |
| WO | PCT/US2021/045553 | 8/2021 |

OTHER PUBLICATIONS

Closed Kinetic Chain Exercises (Wikipedia) 1993, entire document, especially Abstract.
Open Kinetic Chain Exercises (Wikipedia), Oct. 1, 33998, entire document, especially Abstract.
PCT International Search Report and Written Opinion dated Dec. 28, 2021 for PCT/US2021/045553.
U.S. Appl. No. 63/063,984, filed Aug. 11, 2020.

* cited by examiner

DYNAMIC SOCKS AND ASSOCIATED METHODS

CROSS-REFERENCE TO RELATED APPLICATIONS

This application claims the benefit of U.S. Provisional Patent Application No. 63/063,984, which was filed on Aug. 11, 2020, the entire contents of the foregoing patent application hereby expressly incorporated by reference in its entirety.

FIELD OF THE DISCLOSURE

The present disclosure generally relates to dynamic socks and, more specifically, a dynamic compression sock with built-in elastic tensioning bands configured to selectively increase propulsion in human gait (e.g., propulsion socks). The present disclosure also relates to dynamic socks with built-in elastic tensioning bands configured to control inordinate joint motion that can adversely impact gait (e.g., tension socks).

BACKGROUND OF THE DISCLOSURE

Traditionally, socks, pantyhose and athletic pants/leggings have generally been a passive, accommodative garment, knitted or woven to cover the foot and/or legs in order to provide warmth, protection or moisture wicking capability. In recent years, compression socks have been adapted from a medical device designed to treat edema, venous insufficiency, thrombosis, lymphedema or other circulatory disorders, to athletic wear in order to improve blood flow, wick moisture, reduce muscle fatigue and aid in recovery in healthy athletes. Even with recent improvements, traditional socks of all types are still essentially considered a passive foot covering, not performing any work or harnessing the powerful forces generated naturally in human walking, running, or jumping activities.

SUMMARY OF THE DISCLOSURE

It is therefore an object of the present disclosure to provide dynamic socks for athletic, lifestyle or similar activities, or medical applications, where a portion of the human energy expended in walking, running or jumping or similar movements are recovered or harnessed in order to return that captured energy for immediate use in further actions/movements. Although the present disclosure is primarily directed to implementations that take the form of a sock, it is to be understood that the present disclosure may likewise be implemented in alternative forms, e.g., as pantyhose, athletic pants/leggings, or the like.

The above-noted object and other objects are achieved by providing a compression/propulsion sock fabricated from a LYCRA® (Spandex) or other stretchy/elastic material configured, dimensioned and designed to support, surround and/or control one or more parts of the foot, ankle and lower leg. The disclosed sock can advantageously employ advanced weave/band technology and/or elastic material deployment to focus higher compression/tension during the gait cycle in strategic areas of the foot, ankle and/or lower leg in order to increase propulsion/ground force. The exemplary sock does so, at least in part, by loading a spring force during dorsiflexion and releasing that spring force during plantarflexion, using the body's natural lever system by mirroring the function and path of the body's tendon complex responsible for human propulsion. In some embodiments, the disclosed sock can advantageously use these same compressive/elastic tensile bands in an opposite way to limit inordinate foot motion. Both (and additional) functionalities are effectuated in exemplary implementations of the present disclosure.

The present disclosure thus relates to a compression sock or other article of clothing in exemplary implementations that include one or more built-in power or propulsion bands with increased compression/tension capability, individually or in combination, at specific parts of the foot, ankle and/or lower leg to increase the tension during the dorsiflexion moment of the gait cycle to thereby increase the rate, amount and force of plantarflexion. Even a small increase on the force created during plantarflexion can have a material effect on propulsion and yield an advantageous decrease in energy expenditure for equivalent propulsion effect.

In some embodiments, the disclosed sock can include a compression sock of selectively varying compression/tension rates. The disclosed sock can be implemented so as to deliver a desired force level in order to allow and/or deliver proper or desired compression, improve blood flow and reduce swelling in fatigued muscles while not attempting to treat any medical condition. Therefore, in some embodiments, the compression/tension rates provided by the built-in bands can be selectively regulated by the user to achieve the desired or optimal compression or tension for support of the foot/leg.

In some embodiments, the compression level provided by the bands of the exemplary sock can be about, e.g., 8-15 mmHg inclusive, 8-14 mmHg inclusive, 8-13 mmHg inclusive, 8-12 mmHg inclusive, 8-11 mmHg inclusive, 8-10 mmHg inclusive, 8-9 mmHg inclusive, 9-15 mmHg inclusive, 10-15 mmHg inclusive, 11-15 mmHg inclusive, 12-15 mmHg inclusive, 13-15 mmHg inclusive, 14-15 mmHg inclusive, 8 mmHg, 9 mmHg, 10 mmHg, 11 mmHg, 12 mmHg, 13 mmHg, 14 mmHg, 15 mmHg, or the like (pressure measured as millimeters of mercury). This compression level can provide sufficient compression for blood flow and fatigue recovery, while allowing ease of application and comfort for the user during an activity, e.g., normal day-to-day activity and/or athletic activity.

In some embodiments, the material of the sock body can provide a low level of compression of about, e.g., 8-15 mmHg inclusive, 8-14 mmHg inclusive, 8-13 mmHg inclusive, 8-12 mmHg inclusive, 8-11 mmHg inclusive, 8-10 mmHg inclusive, 8-9 mmHg inclusive, 9-15 mmHg inclusive, 10-15 mmHg inclusive, 11-15 mmHg inclusive, 12-15 mmHg inclusive, 13-15 mmHg inclusive, 14-15 mmHg inclusive, 8 mmHg, 9 mmHg, 10 mmHg, 11 mmHg, 12 mmHg, 13 mmHg, 14 mmHg, 15 mmHg, or the like, and the bands formed on or in the material of the sock can provide a medium to high level of tension of about, e.g., 15-20 mmHg inclusive, 15-19 mmHg inclusive, 15-18 mmHg inclusive, 15-17 mmHg inclusive, 15-16 mmHg inclusive, 16-20 mmHg inclusive, 17-20 mmHg inclusive, 18-20 mmHg inclusive, 19-20 mmHg inclusive, 15 mmHg, 16 mmHg, 17 mmHg, 18 mmHg, 19 mmHg, 20 mmHg, or the like.

In accordance with embodiments of the present disclosure, an exemplary dynamic sock (e.g., a propulsion sock) is provided. The sock includes a main body section configured to cover at least a portion of a foot and a lower leg of a user. The main body section can be fabricated from a material configured to impart a compressive force against the portion of the foot and the lower leg of the user. The sock includes a propulsion band coupled to or integrated into the main body section to define a band path. The band path traverses or extends from a first section superior to metatarsals heads, traverses medially and laterally to the metatarsal heads in a second section, further traverses inferior to an arch of a foot to merge into a single band in a third section, and extends posteriorly underneath a heel section in a fourth section. The propulsion band is adapted to increase propulsion at plantarflexion.

The band path extends superiorly up a back of a calf in a fifth section. The band path splits into a substantially V-shaped section at or near an upper part of the calf in a sixth section. The band path wraps around the leg medially and laterally, joining and terminating at a shin inferior to a patella of the user in a seventh section.

A compression value of the propulsion band is greater than the main body section. In some embodiments, the compression value of the main body section can be about 8 mmHg to about 15 mmHg, inclusive, and the compression value of the propulsion band can be about 15 mmHg to about 20 mmHg, inclusive. In some embodiments, the main body section can be in a form of a sock. In some embodiments, the main body section can be pantyhose, athletic pants, or athletic leggings.

The propulsion band is elastic in a first direction having a stretch ratio of about ±50-80% (e.g., 50-80% inclusive, 50-75% inclusive, 50-70% inclusive, 50-65% inclusive, 50-60% inclusive, 50-55% inclusive, 55-80% inclusive, 60-80% inclusive, 65-80% inclusive, 70-80% inclusive, 75-80% inclusive, 50%, 55%, 60%, 65%, 70%, 75%, 80%, or the like), and resistant in a second direction opposite at any angle to the first direction and having a stretch ratio of about ±20-40% (e.g., 20-40% inclusive, 20-35% inclusive, 20-30% inclusive, 20-25% inclusive, 25-40% inclusive, 30-40% inclusive, 35-40% inclusive, 20%, 25%, 30%, 35%, 40%, or the like). These ratios can be applicable to the alternative propulsion and tension bands discussed herein.

In some embodiments, the main body section can be woven and the propulsion band can be integrated into the main body section by stitching an elastic thread into the main body section along the band path. The main body section can include a low compression or density weave and the propulsion band can include a high compression or density weave. In some embodiments, the propulsion band can be integrated into the main body section by Jacquard knitting an elastic thread into the main body section at the band path. In some embodiments, the propulsion band defines an elongated elastic material coupled to an outer surface of the main body section along the band path.

In some embodiments, the propulsion band can be moveable relative to the main body section to allow for reconfiguration of the band path. The propulsion band can moveable relative to the main body section to allow for an increase or decrease in tension provided by the propulsion band. In some embodiments, the main body section can include a pocket formed at or near a shin area, the pocket configured to removably receive a shin guard.

In some embodiments, the main body section can fabricated from spandex. In some embodiments, the propulsion band can be fabricated from a material including about 70-90% polyester and about 10-30% rubber. The propulsion band is adapted to plantarflex a foot of the user in an open chain, and is adapted to be loaded in dorsiflexion in a closed chain to return energy in plantarflexion.

In accordance with embodiments of the present disclosure, an exemplary method of providing plantarflexion propulsion to a user is provided. The method includes providing a dynamic sock including a main body section and a propulsion band coupled to or integrated into the main body section to define a band path. The main body section is configured to cover at least a portion of a foot and a lower leg of a user. The band path extends from a first section superior to metatarsals heads, traverses medially and laterally to the metatarsal heads in a second section, further traverses inferior to an arch of a foot to merge into a single band in a third section, and extends posteriorly underneath a heel section in a fourth section. The method includes imparting a compressive force against the portion of the foot and the lower leg of the user with the main body section. The method includes increasing propulsion at plantarflexion with the propulsion band.

In accordance with embodiments of the present disclosure, an exemplary dynamic sock (e.g., a propulsion sock) is provided. The sock includes a main body section configured to cover at least a portion of a foot and a lower leg of a user, the main body section fabricated from a material configured to impart a compressive force against the portion of the foot and the lower leg of the user. The sock includes a propulsion band coupled to or integrated into the main body section to define a band path. The band path extends from a first section at or near a superior aspect of a first metatarsal, and extends laterally and superior to a fifth metatarsal in a second section. The propulsion band is adapted to increase propulsion at plantarflexion.

The band path extends medially and posteriorly under an arch of a foot in a third section, and extends superiorly and posteriorly toward a medial malleolus in a fourth section. The band path extends superiorly towards an upper part of a calf in a fifth section. The band path wraps around a lateral gastrocnemius in a sixth section, and terminates at a lateral aspect of the calf in a seventh section.

A compression value of the propulsion band is greater than the main body section. In some embodiments, the compression value of the main body section can be about 8 mmHg to about 15 mmHg, inclusive, and the compression value of the propulsion band can be about 15 mmHg to about 20 mmHg, inclusive. In some embodiments, the main body section can be in a form of a sock. In some embodiments, the main body section can be pantyhose, athletic pants, or athletic leggings.

The propulsion band is elastic in a first direction having a stretch ratio of about ±50-80%, and resistant in a second direction opposite at any angle to the first direction and having a stretch ratio of about ±20-40%. In some embodiments, the main body section can be woven and the propulsion band can be integrated into the main body section by stitching an elastic thread into the main body section along the band path. The main body section can include a low compression or density weave and the propulsion band can include a high compression or density weave. In some embodiments, the propulsion band can be integrated into the main body section by Jacquard knitting an elastic thread into the main body section at the band path. In some embodiments, the propulsion band defines an elongated elastic material coupled to an outer surface of the main body section along the band path.

In some embodiments, the propulsion band can be moveable relative to the main body section to allow for reconfiguration of the band path. The propulsion band can moveable relative to the main body section to allow for an increase or decrease in tension provided by the propulsion band. In some embodiments, the main body section can include a pocket formed at or near a shin area, the pocket configured to removably receive a shin guard.

In some embodiments, the main body section can fabricated from spandex. In some embodiments, the propulsion band can be fabricated from a material including about 70-90% polyester and about 10-30% rubber. The propulsion band is adapted to plantarflex a foot of the user in an open chain, and is adapted to be loaded in dorsiflexion in a closed chain to return energy in plantarflexion.

In accordance with embodiments of the present disclosure, an exemplary method of providing plantarflexion propulsion to a user is provided. The method includes providing a dynamic sock including a main body section and a propulsion band coupled to or integrated into the main body section to define a band path. The main body section is configured to cover at least a portion of a foot and a lower leg of a user. The band path extends from a first section at or near a superior aspect of a first metatarsal, and extends laterally and superior to a fifth metatarsal in a second section. The method includes imparting a compressive force against the portion of the foot and the lower leg of the user with the main body section. The method includes increasing propulsion at plantarflexion with the propulsion band.

In accordance with embodiments of the present disclosure, an exemplary dynamic sock (e.g., a propulsion sock) is provided. The sock includes a main body section configured to cover at least a portion of a foot and a lower leg of a user. The main body section is fabricated from a material configured to impart a compressive force against the portion of the foot and the lower leg of the user. The sock includes a propulsion band coupled to or integrated into the main body section to define a band path. The band path extends from a first section superior to a first metatarsal, extends laterally and posteriorly to a fifth metatarsal in a second section, and wraps inferiorly underneath the fifth metatarsal in a third section. The propulsion band is adapted to increase propulsion at plantarflexion.

The band path extends posteriorly and medially under an arch in a fourth section, and extends superiorly and posteriorly around an instep in a fifth section. The band path extends across and inferior to a lateral malleolus in a sixth section, and extends inferiorly under a heel in a seventh section. The band path extends superiorly up a posterior aspect of a calf in an eighth section, and splits into a V-shaped section at or near a top of the calf in a ninth section.

A compression value of the propulsion band is greater than the main body section. In some embodiments, the compression value of the main body section can be about 8 mmHg to about 15 mmHg, inclusive, and the compression value of the propulsion band can be about 15 mmHg to about 20 mmHg, inclusive. In some embodiments, the main body section can be in a form of a sock. In some embodiments, the main body section can be pantyhose, athletic pants, or athletic leggings.

The propulsion band is elastic in a first direction having a stretch ratio of about ±50-80%, and resistant in a second direction opposite at any angle to the first direction and having a stretch ratio of about ±20-40%. In some embodiments, the main body section can be woven and the propulsion band can be integrated into the main body section by stitching an elastic thread into the main body section along the band path. The main body section can include a low compression or density weave and the propulsion band can include a high compression or density weave. In some embodiments, the propulsion band can be integrated into the main body section by Jacquard knitting an elastic thread into the main body section at the band path. In some embodiments, the propulsion band defines an elongated elastic material coupled to an outer surface of the main body section along the band path.

In some embodiments, the propulsion band can be moveable relative to the main body section to allow for reconfiguration of the band path. The propulsion band can moveable relative to the main body section to allow for an increase or decrease in tension provided by the propulsion band. In some embodiments, the main body section can include a pocket formed at or near a shin area, the pocket configured to removably receive a shin guard.

In some embodiments, the main body section can fabricated from spandex. In some embodiments, the propulsion band can be fabricated from a material including about 70-90% polyester and about 10-30% rubber. The propulsion band is adapted to plantarflex a foot of the user in an open chain, and is adapted to be loaded in dorsiflexion in a closed chain to return energy in plantarflexion.

In accordance with embodiments of the present disclosure, an exemplary method of providing plantarflexion propulsion to a user is provided. The method includes providing a dynamic sock including a main body section and a propulsion band coupled to or integrated into the main body section to define a band path. The main body section is configured to cover at least a portion of a foot and a lower leg of a user. The band path extends from a first section superior to a first metatarsal, extends laterally and posteriorly to a fifth metatarsal in a second section, and wraps inferiorly underneath the fifth metatarsal in a third section. The method includes imparting a compressive force against the portion of the foot and the lower leg of the user with the main body section. The method includes increasing propulsion at plantarflexion with the propulsion band.

In accordance with embodiments of the present disclosure, an exemplary dynamic sock (e.g., a tension sock) is provided. The sock includes a main body section configured to cover at least a portion of a foot and a lower leg of a user. The main body section is fabricated from a material configured to impart a compressive force against the portion of the foot and the lower leg of the user. The sock includes a tension band coupled to or integrated into the main body section to define a band path. The band path extends from a first section under metatarsal heads, extends superiorly, medially and laterally in a second section, and joins over metatarsals in a third section. The tension band is adapted to increase dorsiflexion of a forefoot.

The band path extends up an instep of a foot in a fourth section, and extends superiorly over a front of an ankle and up over a shin in a fifth section. The band path splits inferior to a kneecap in a sixth section. The band path extends medially and laterally around a calf to join anterior of the shin or at a posterior aspect of an upper calf in a seventh section.

A compression value of the tension band is greater than the main body section. In some embodiments, the compression value of the main body section can be about 8 mmHg to about 15 mmHg, inclusive, and the compression value of the tension band can be about 15 mmHg to about 20 mmHg, inclusive. In some embodiments, the main body section can be in a form of a sock. In some embodiments, the main body section can be pantyhose, athletic pants, or athletic leggings.

The tension band is elastic in a first direction having a stretch ratio of about ±50-80%, and resistant in a second direction opposite at any angle to the first direction and having a stretch ratio of about ±20-40%. In some embodiments, the main body section can be woven and the tension band can be integrated into the main body section by stitching an elastic thread into the main body section along the band path. The main body section can include a low compression or density weave and the tension band can include a high compression or density weave. In some embodiments, the tension band can be integrated into the main body section by Jacquard knitting an elastic thread into the main body section at the band path. In some embodiments, the tension band can define an elongated elastic material coupled to an outer surface of the main body section along the band path.

In some embodiments, the tension band can be moveable relative to the main body section to allow for reconfiguration of the band path. The tension band can be moveable relative to the main body section to allow for an increase or decrease in tension provided by the tension band. In some embodiments, the main body section can include a pocket formed at or near a shin area, the pocket configured to removably receive a shin guard. In some embodiments, the main body section can be fabricated from spandex. In some embodiments, the tension band can be fabricated from a material including about 70-90% polyester and about 10-30% rubber. The tension band is adapted to maintain the foot in a dorsiflexed position.

In accordance with embodiments of the present disclosure, an exemplary method of providing dorsiflexion support to a user is provided. The method includes providing a dynamic sock including a main body section and a tension band coupled to or integrated into the main body section to define a band path. The main body section is configured to cover at least a portion of a foot and a lower leg of a user. The band path extends from a first section under metatarsal heads, extends superiorly, medially and laterally in a second section, and joins over metatarsals in a third section. The method includes imparting a compressive force against the portion of the foot and the lower leg of the user with the main body section. The method includes increasing tension for dorsiflexion of a forefoot with the tension band. In accordance with embodiments of the present disclosure, an exemplary dynamic sock (e.g., a tension sock) is provided. The sock includes a main body section configured to cover at least a portion of a foot and a lower leg of a user. The main body section is fabricated from a material configured to impart a compressive force against the portion of the foot and the lower leg of the user. The sock includes a tension band coupled to or integrated into the main body section to define a band path. The band path extends from a first section under toes, extends superiorly over a top of the toes in a second section, and extends over a superior aspect of metatarsals in a third section. The tension band is adapted to increase dorsiflexion of a forefoot and the toes.

The band path extends up an instep of a foot in a fourth section, and extends superiorly over a front of an ankle in a fifth section. The band path extends over a shin in a sixth section, and extends anterior to an aspect of a tibia where the tension band splits inferior to a kneecap in a seventh section. The band path extends medially and laterally around a calf in an eighth section, and joins at a posterior aspect of an upper calf in a ninth section.

A compression value of the tension band is greater than the main body section. In some embodiments, the compression value of the main body section can be about 8 mmHg to about 15 mmHg, inclusive, and the compression value of the tension band can be about 15 mmHg to about 20 mmHg, inclusive. In some embodiments, the main body section can be in a form of a sock. In some embodiments, the main body section can be pantyhose, athletic pants, or athletic leggings.

The tension band is elastic in a first direction having a stretch ratio of about ±50-80%, and resistant in a second direction opposite at any angle to the first direction and having a stretch ratio of about ±20-40%. In some embodiments, the main body section can be woven and the tension band can be integrated into the main body section by stitching an elastic thread into the main body section along the band path. The main body section can include a low compression or density weave and the tension band can include a high compression or density weave. In some embodiments, the tension band can be integrated into the main body section by Jacquard knitting an elastic thread into the main body section at the band path. In some embodiments, the tension band can define an elongated elastic material coupled to an outer surface of the main body section along the band path.

In some embodiments, the tension band can be moveable relative to the main body section to allow for reconfiguration of the band path. The tension band can be moveable relative to the main body section to allow for an increase or decrease in tension provided by the tension band. In some embodiments, the main body section can include a pocket formed at or near a shin area, the pocket configured to removably receive a shin guard. In some embodiments, the main body section can be fabricated from spandex. In some embodiments, the tension band can be fabricated from a material including about 70-90% polyester and about 10-30% rubber. The tension band is adapted to maintain the foot in a dorsiflexed position.

In accordance with embodiments of the present disclosure, an exemplary method of providing dorsiflexion support to a user is provided. The method includes providing a dynamic sock including a main body section and a tension band coupled to or integrated into the main body section to define a band path. The main body section is configured to cover at least a portion of a foot and a lower leg of a user. The band path extends from a first section under toes, extends superiorly over a top of the toes in a second section, and extends over a superior aspect of metatarsals in a third section. The method includes imparting a compressive force against the portion of the foot and the lower leg of the user with the main body section. The method includes increasing tension for dorsiflexion of a forefoot and the toes with the tension band.

In accordance with embodiments of the present disclosure, an exemplary dynamic sock (e.g., a tension sock) is provided. The sock includes a main body section configured to cover at least a portion of a foot and a lower leg of a user. The main body section is fabricated from a material configured to impart a compressive force against the portion of the foot and the lower leg of the user. The sock includes a tension band coupled to or integrated into the main body section to define a band path. The band path extends from a first section at a front shin area, extends inferior to a patella in a second section, and extends laterally and inferiorly around a lateral side of a calf in a third section. The tension band is adapted to pull and guide a big toe of the user.

The band path extends laterally and inferiorly around an ankle in a fourth section, and extends medially around a back of a heel in fifth section. The band path extends inferior to a medial malleolus in a sixth section, and extends straight forward on a medial side of a foot in a seventh section. The band path terminates at a distal medial aspect of the big toe in an eighth section.

A compression value of the tension band is greater than the main body section. In some embodiments, the compression value of the main body section can be about 8 mmHg to about 15 mmHg, inclusive, and the compression value of the tension band can be about 15 mmHg to about 20 mmHg, inclusive. In some embodiments, the main body section can be in a form of a sock. In some embodiments, the main body section can be pantyhose, athletic pants, or athletic leggings.

The tension band is elastic in a first direction having a stretch ratio of about ±50-80%, and resistant in a second direction opposite at any angle to the first direction and having a stretch ratio of about ±20-40%. In some embodiments, the main body section can be woven and the tension band can be integrated into the main body section by stitching an elastic thread into the main body section along the band path. The main body section can include a low compression or density weave and the tension band can include a high compression or density weave. In some embodiments, the tension band can be integrated into the main body section by Jacquard knitting an elastic thread into the main body section at the band path. In some embodiments, the tension band can define an elongated elastic material coupled to an outer surface of the main body section along the band path.

In some embodiments, the tension band can be moveable relative to the main body section to allow for reconfiguration of the band path. The tension band can be moveable relative to the main body section to allow for an increase or decrease in tension provided by the tension band. In some embodiments, the main body section can include a pocket formed at or near a shin area, the pocket configured to removably receive a shin guard. In some embodiments, the main body section can be fabricated from spandex. In some embodiments, the tension band can be fabricated from a material including about 70-90% polyester and about 10-30% rubber. The tension band is adapted to maintain the foot in a dorsiflexed position.

In accordance with embodiments of the present disclosure, an exemplary method of providing hallux valgus support to a user is provided. The method includes providing a dynamic sock including a main body section and a tension band coupled to or integrated into the main body section to define a band path. The main body section is configured to cover at least a portion of a foot and a lower leg of a user. The band path extends from a first section at a front shin area, extends inferior to a patella in a second section, and extends laterally and inferiorly around a lateral side of a calf in a third section. The method includes imparting a compressive force against the portion of the foot and the lower leg of the user with the main body section. The method includes pulling laterally on a big toe of the user with the tension band.

It should be noted that, although the primary/sole purpose of the exemplary sock or other article of clothing is not compression (as with traditional compression socks), the exemplary sock will typically have compression characteristics that may vary at strategic areas of the garment in combination with strategic areas of tension to support the user's foot and/or leg.

Any combination or permutation of embodiments is envisioned. Additional features, functions and benefits of the disclosed dynamic compression socks/garments will be apparent from the description which follows, particularly when read in conjunction with the appended figures.

BRIEF DESCRIPTION OF THE DRAWINGS

Features and aspects of embodiments are described below with reference to the accompanying drawings, in which elements are not necessarily depicted to scale. It is to be noted that the various steps, features and combinations of steps/features described below and illustrated in the figures can be arranged and organized differently to result in embodiments which are still within the scope of the present disclosure. To assist those of ordinary skill in the art in making and using the disclosed dynamic compression socks, reference is made to the appended figures, wherein.

DETAILED DESCRIPTION OF THE DISCLOSURE

Propulsion Band Technology and Its Effects on Joint Function

Figure 1A:
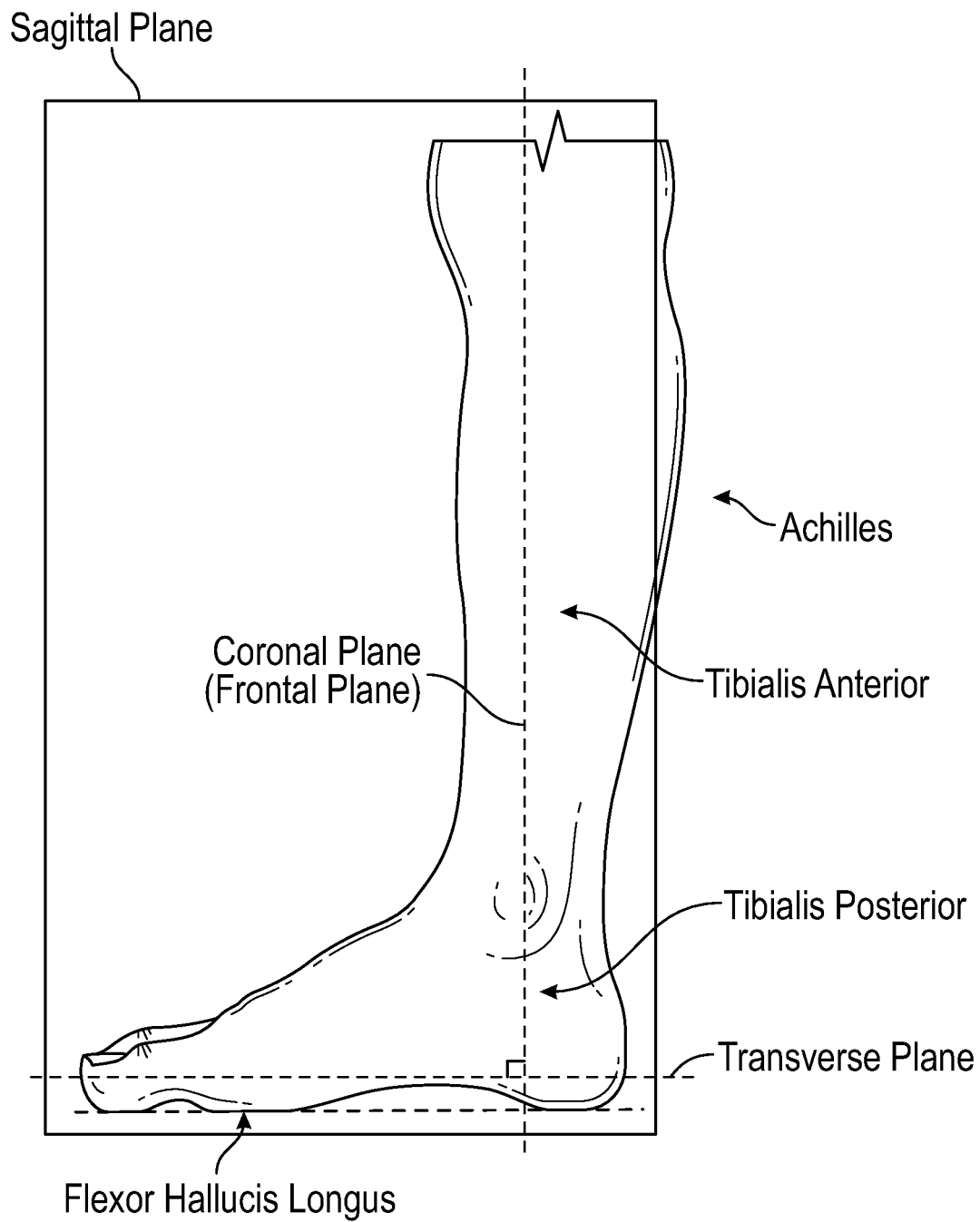
FIG. 1A is a diagrammatic, inner side view of a right leg of a user.
Figure 1B:
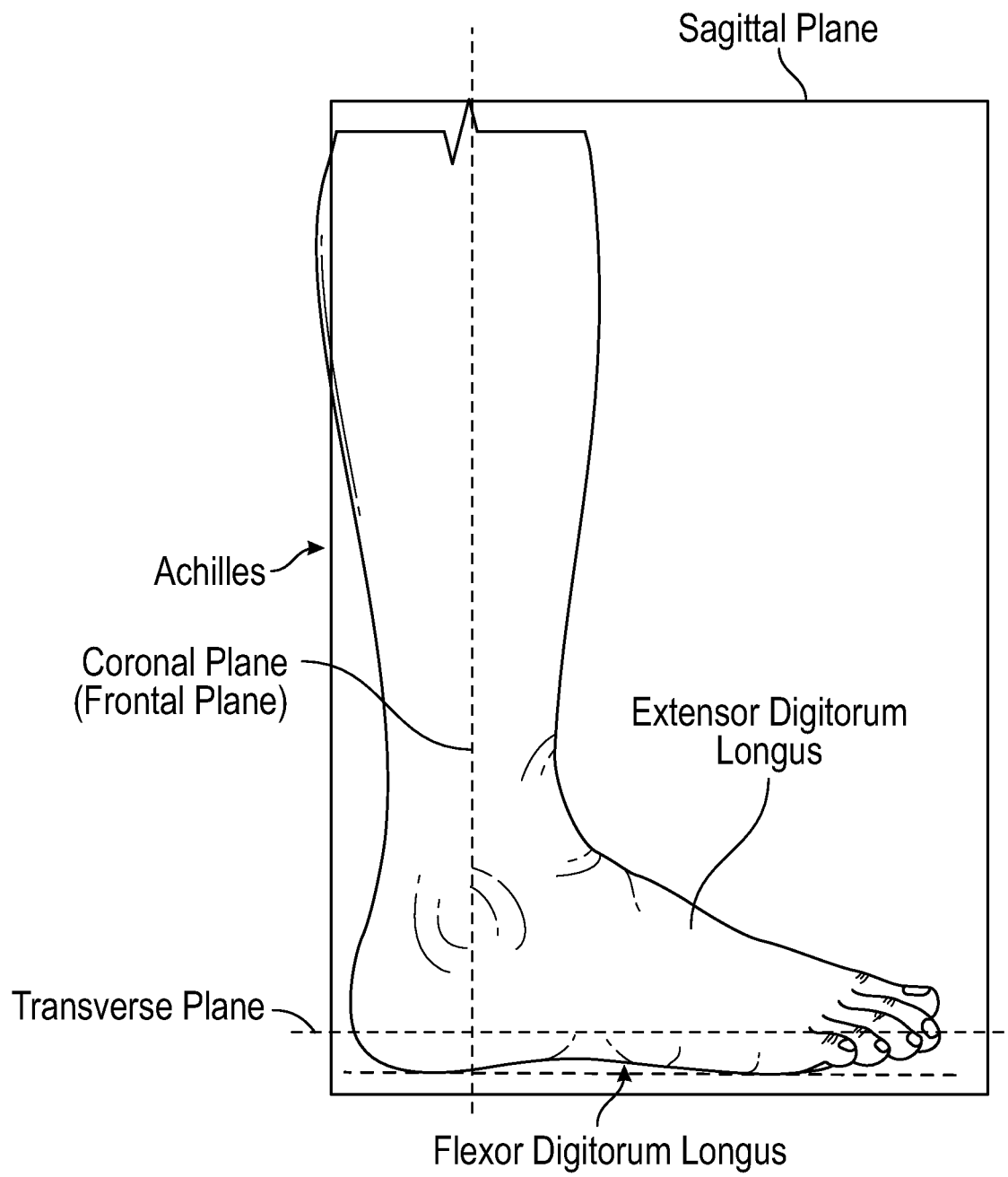
FIG. 1B is a diagrammatic, outer side view of a right leg of a user.

FIGS. 1A-1B are diagrammatic, inner and outer side views of a right leg of a user. FIGS. 1A-1B show the sagittal plane, the coronal or frontal plane, and the transverse plane. The sagittal plane is a vertical plane that generally extends from front to back, dividing each leg into right and left sides. The coronal or frontal plane is a vertical plane that generally extends from side to side, dividing each leg into anterior and posterior portions. The transverse plane is a horizontal plane that divides each leg into upper and lower portions. FIGS. 1A-1B identify the general locations of the Achilles' tendon, the Tibialis anterior, the Tibialis posterior, the Flexor Hallucis Longus, the Extensor Digitorum Longus, and the Flexor Digitorum Longus.

Human joints that impact propulsion operate in the sagittal plane (up or down line). In the metatarsals, ankles, knees and hips, any forward and/or backward movement parallel to this line occurs in the sagittal plane. An example of sagittal plane work is demonstrated when an individual raises the heels off of the ground and stands on their toes by bending at the ankles when pushing off the ground, or by bending the knees to run or jump. Traditional compression socks generally work only in the transverse and frontal planes to aid the body in muscle fatigue, blood flow and muscle recovery; that is, they are designed to focus compression in, against the foot and leg. Because the pressure from a traditional compression sock is in towards/against the leg, it cannot harness any energy in the sagittal plane of the body, the plane that the joints of the leg operate in. The body therefore cannot benefit substantially from any work in these planes. As a result, by definition, a sock to affect propulsion must operate in the sagittal plane to affect propulsion.

Tendons and muscles also mainly operate in the sagittal plane (up and/or down) in order to accomplish a specific task or quantity of work. It is mainly in the sagittal plane that a mass can accelerate, decelerate, lift, run or jump. The other planes (frontal and transverse) are generally more responsible for torquing, twisting or lateral motions.

The described invention includes a dynamic sock (e.g., a propulsion sock, a tension sock, or the like) with a built-in power band possessing increased tension capability at specific parts of the foot, ankle and/or lower leg to increase the amount of stored energy at the dorsiflexion moment of the gait cycle to thereby increase the rate, amount and force of plantarflexion.

By loading a spring during dorsiflexion, plantarflexion force is increased. This increase in plantarflexion force can result in increased ground force, thereby increasing propulsion in human gait. As a result of increasing the plantarflexion force, eccentric loading of the joints is decreased up to the amount of plantarflexion force. This decreased joint loading can result also in a decrease of G-force upon landing.

Most of the described properties would benefit an athlete interested in increasing power during running or jumping. However, these propulsive and compressive properties would also help the general public, especially those who could benefit from increased "push" in walking, making exercise easier.

The described sock includes a compression/tension sock of varying compression and tension weaves selectively combined with elasticized propulsion bands. The proposed invention is described in the lowest mmHg range in order to allow proper compression (e.g., about 8-15 mmHg), improve blood flow and reduce swelling in fatigued muscles while not attempting to treat any medical condition. These bands may be incorporated into the weave of the sock, sewn into the sock itself or attached to the sock in any number of ways. For example, the sock can be prefabricated and the band can be attached to the sock in selective areas via, e.g., adhesive, heat welding, sewing, or the like.

In some embodiments, the compression rates for the described invention may be in the mid or mild range (e.g., about 8-15 mmHg). In some embodiments, the compression and/or tension rates may be in a higher range (e.g., about 15-20 mmHg) at specific points to facilitate joint control. These compression and/or tension rates provide sufficient compression for blood flow and fatigue recovery while allowing ease of application and comfort for the user during athletic activity. The exemplary sock is not necessarily designed to be a medical treatment for cases of edema, venous insufficiency, thrombosis, lymphedema, phlebitis, or any other circulatory pathology diagnosed by a medical doctor, although it may indirectly alleviate some related symptoms.

The exemplary sock incorporates propulsion and/or tension bands at strategic points through various pathways of the sock, designed to store and release energy during walking, running and/or jumping movements. These propulsion and/or tension bands may be fabricated of any variety of materials capable of stretching and storing energy and then returning the stored energy while returning to their unstretched state. In some embodiments, the bands may be composed of a knit elastic material made of about 85% polyester and about 15% rubber, but may also be made of any other stretchy material that can store or return energy efficiently and effectively.

In some embodiments, the knit elastic material can be made of about, e.g., 70-90% inclusive, 70-89% inclusive, 70-88% inclusive, 70-87% inclusive, 70-86% inclusive, 70-85% inclusive, 70-84% inclusive, 70-83% inclusive, 70-82% inclusive, 70-81% inclusive, 70-80% inclusive, 70-79% inclusive, 70-78% inclusive, 70-77% inclusive, 70-76% inclusive, 70-75% inclusive, 70-74% inclusive, 70-73% inclusive, 70-72% inclusive, 70-71% inclusive, 71-90% inclusive, 72-90% inclusive, 73-90% inclusive, 74-90% inclusive, 75-90% inclusive, 76-90% inclusive, 77-90% inclusive, 78-90% inclusive, 79-90% inclusive, 80-90% inclusive, 81-90% inclusive, 82-90% inclusive, 83-90% inclusive, 84-90% inclusive, 85-90% inclusive, 86-90% inclusive, 87-90% inclusive, 88-90% inclusive, 89-90% inclusive, 70%, 71%, 72%, 73%, 74%, 75%, 76%, 77%, 78%, 79%, 80%, 81%, 83%, 83%, 84%, 85%, 86%, 87%, 88%, 89%, 90%, or the like, polyester. In some embodiments, the knit elastic material can be made of about, e.g., 10-30% inclusive, 10-29% inclusive, 10-28% inclusive, 10-27% inclusive, 10-26% inclusive, 10-25% inclusive, 10-24% inclusive, 10-23% inclusive, 10-22% inclusive, 10-21% inclusive, 10-20% inclusive, 10-19% inclusive, 10-18% inclusive, 10-17% inclusive, 10-16% inclusive, 10-15% inclusive, 10-14% inclusive, 10-13% inclusive, 10-12% inclusive, 10-11% inclusive, 11-30% inclusive, 12-30% inclusive, 13-30% inclusive, 14-30% inclusive, 15-30% inclusive, 16-30% inclusive, 17-30% inclusive, 18-30% inclusive, 19-30% inclusive, 20-30% inclusive, 21-30% inclusive, 22-30% inclusive, 23-30% inclusive, 24-30% inclusive, 25-30% inclusive, 26-30% inclusive, 27-30% inclusive, 28-30% inclusive, 29-30% inclusive, 10%, 11%, 12%, 13%, 14%, 15%, 16%, 17%, 18%, 19%, 20%, 21%, 22%, 23%, 24%, 25%, 26%, 27%, 28%, 29%, 30%, or the like, rubber.

These bands may be attached to the sock by various methods including but not limited to, sewing with (elastic) thread, heat application, adhesive application or other techniques that will allow the bands to adhere to the sock, tolerate repeated washing and yet still be comfortable for the wearer while providing the intended compression and/or tension forces. In some embodiments, the bands can be composed of the same material that the sock is made from but in a weave that is biased and tighter from the rest of the sock in order to facilitate energy storage and return.

In some embodiments, the body of the compression sock can be fabricated out of a fabric such as but not limited to LYCRA® (Spandex) with a composition and properties as follows:

TABLE 1

| LYCRA ® Composition and Properties | |
|---|---|
| Fabric also known as: | Spandex, elastane |
| Fabric composition: | Polyether-polyurea copolymer |
| Fabric breathability: | High breathability |
| Moisture-wicking abilities: | High |

TABLE 1-continued

LYCRA® Composition and Properties

| | |
|---|---|
| Heat retention abilities: | Low |
| Stretchability (give): | Extraordinarily high |

In some embodiments, the propulsion and/or tension bands can be fabricated out of a fabric, such as but not limited to, about 69% polyester and about 31% rubber with a heavy knit of high elasticity. The band can be about, e.g., 1 inch, 2 inches, 3 inches, or 4 inches in width. The band can be a substantially flat elastic and can extend in one direction. Therefore, the band does not narrow when stretched. In some embodiments, the band can be fabricated using a Jacquard method of knitting. This method can incorporate the weaving of different material and tension threads using a computer controlled Jacquard knitting machine giving the sock a "scrunched" appearance when off the foot/leg. In some embodiments, the body of the sock, the propulsion band and/or the tension band can be fabricated from, e.g., cotton, nylon, polyester, acrylic, spandex, combinations thereof, or the like.

Anatomical Assist of Propulsive Tendons of Lower Limb

Each of the propulsive band configurations discussed herein are designed to mirror (or substantially mirror) the path of the main propulsive tendons of the foot, ankle and lower leg. By mirroring the path of these tendons, the bands can assist such tendons in the direction of their respective functions. Each band pathway that is described herein has the corresponding tendon that it will assist in parenthesis.

In some embodiments, the described propulsion bands can include or be fabricated from a higher weave density instead of elastic bands. Such weave is intended to pull in the sagittal plane. The high compression bands (e.g., about 15-20 mmHg) should be offset on the opposing side with a very low compression/stretchy material (e.g., about 8-15 mmHg) in order to allow the bands to control the desired joint. As the high compression bands pull the foot into the desired direction, the low compression material on the opposing side must give way in an equal amount in order to allow the higher compression bands to perform their intended function. If the body of the sock itself was fabricated from a similar compression/tension on all sides, the pull would be the same on both sides and no work would be performed by the sock.

Concept of Joint Assist in Dynamic Sportswear

The concept of joint assist is the basis of dynamic garment technology. In the case of dynamic socks, the intrinsic bands gently guide the forefoot into plantarflexion when unweighted and thereby store energy upon weight-bearing (dorsiflexion), then release energy in plantarflexion during gait. When the foot leaves the ground and is unweighted, the sock adds extra spring potential upon weight-bearing at the ankle joint. When the tibia is over the ankle, the forefoot is loaded by the sock. When the tibia passes over the ankle and the talocrural angle is less than 90 degrees, similar to when an athlete is crouched and ready to sprint, that spring is amplified. The more acute the angle of the tibia/ankle, the more potential energy is loaded in the sock because the propulsion band is stretched further. The exemplary propulsion sock discussed herein is uniquely designed to plantarflex the foot in the open chain. In the closed chain, the sock is loaded in dorsiflexion and returns energy in plantarflexion.

Joint assist is made possible by the concept of propulsion bands, which have the unique property of being very elastic in one direction and very resistant in another, to accomplish a given work. As used herein, the term "slightly elastic" or "slightly stretchy" refers to a material having an approximately 20% stretch ratio, meaning that a 10 cm piece of material will stretch to approximately 12 cm maximum. As used herein, the term "stretchy elastic" refers to a material having a stretch ratio of about 50%, meaning that a 10 cm piece of material will stretch to approximately 15 cm maximum. As used herein, the term "very stretchy" or "very elastic" refers to a material having a stretch ratio of about 80-100%. The terms "elastic" and "resistant" are used as inverses of each other in that a very stretchy material has a low resistance, and vice versa. In this way, the garment that the bands are part of can be easily put on and comfortable to wear, but be resistant in a different plane in order to store and release energy in the desired direction.

Instead of having the properties of a traditional compression sock material which applies pressure fairly consistently against the leg in one plane, the described propulsion sock applies tensile force in the band area and medium compression against the leg. These bands are highly resistant in the sagittal plane when stretching against themselves.

Proprioceptive Neuromuscular Facilitation

The concept of proprioceptive neuromuscular facilitation (PNF) is well-known in the practice of physical therapy. PNF involves repeated muscle activation of the limbs by quick stretching, traction, approximation, and maximal manual resistance in functional directions (i.e. spiral and diagonal patterns) to assist with motor relearning and increasing sensory input. Due to the compressive and dynamic nature of the exemplary dynamic propulsion socks, the socks can facilitate the normal neuromuscular response of the muscles of the lower leg (similar to kinesiotape) by providing by tactile stimulation and increased tension in the tissues they contact. This stimulation increases the response from the muscle spindle and augments the stretch reflex in the calf musculature. Since the timing of the stimulation is in sync with the normal physiological cues for muscle contraction during acceleration and jumping, dynamic propulsion socks perform a proprioceptive neuromuscular facilitation function which can improve the performance of the athlete when performing these activities.

Propulsion Bands

Referring now to the figures in detail, where like reference numbers refer to like elements throughout the several views, exemplary dynamic compression socks are provided. Although different configurations or designs of the dynamic compression socks are illustrated and discussed, it should be understood that one or more portions of the configurations or designs of such socks could be combined or interchanged, and such alternative configurations are envisioned as part of the described designs. As an example, one or more propulsion bands of the different designs could be combined into a single sock to provide multiple different support elements to the user. As a further example, one or more propulsion bands could be combined with one or more tension bands to provide different types of support to the user. In each of the embodiments discussed herein, similar configurations may be applicable to pantyhose, athletic pants/leggings, or similar articles of clothing for a human being. In general, the socks are envisioned to be approximately knee high, although the present disclosure is not limited by or to such implementation.

In each of the propulsion configurations (FIGS. 2-5), the propulsion/power band configurations are intended to control the ankle joint and assist the ankle joint in loading a tensile force in dorsiflexion and releasing stored energy at plantarflexion. The energy that is stored by the bands in each of the configurations in the normal process of walking, running or jumping is enhanced by the natural lockup function of the midfoot in combination with the tibia/fibula complex. The farther the tib/fib progresses past the midfoot in midstance and the angle of the tibia to the foot becomes more acute, the more the bands stretch at the posterior aspect of the sock and the more potential energy is loaded at the arch and heel, pulling down the forefoot and amplifying the effect of plantarflexion propulsion.

Each of the propulsion sock configurations can be available with an option for sports in which athletes require shin or leg guards. In such embodiments, the sock designs can be available with a pocket formed in the shin or lateral leg area for the insertion of a carbon fiber or other similar material in a layered or non-layered configuration (see, e.g., pocket 136 in FIG. 2). This shin/leg guard can be made of a lightweight carbon fiber using layering technology. This technology may feature a flexible carbon fiber plate; however, it may also be made of any material designed to absorb shock on impact. The flex can attenuate the shock, protecting the athlete from impact, similar to a carbon fiber race car protecting the driver. The pocket for the shin or leg plate can include an opposing pocket configuration where the bottom of the guard would slide into the bottom pocket and the top inverted pocket, would slide over the top of the guard. If the guard is fabricated of carbon fiber, it could feature a layered design where the guard is thickest over the shin and then gradually gets thinner as it extends medially and laterally. In some embodiments, the pocket for the carbon fiber plate can be located on the outside of the shin for a right or left-handed batter in baseball. In some embodiments, the shin/leg plate can have a curved or rectangular shape with rounded corners and can include a curved design for easy insertion. The shin/leg plate can be available in varying sizes, e.g., men's, women's, small, medium, large, and XL.

Figure 2:
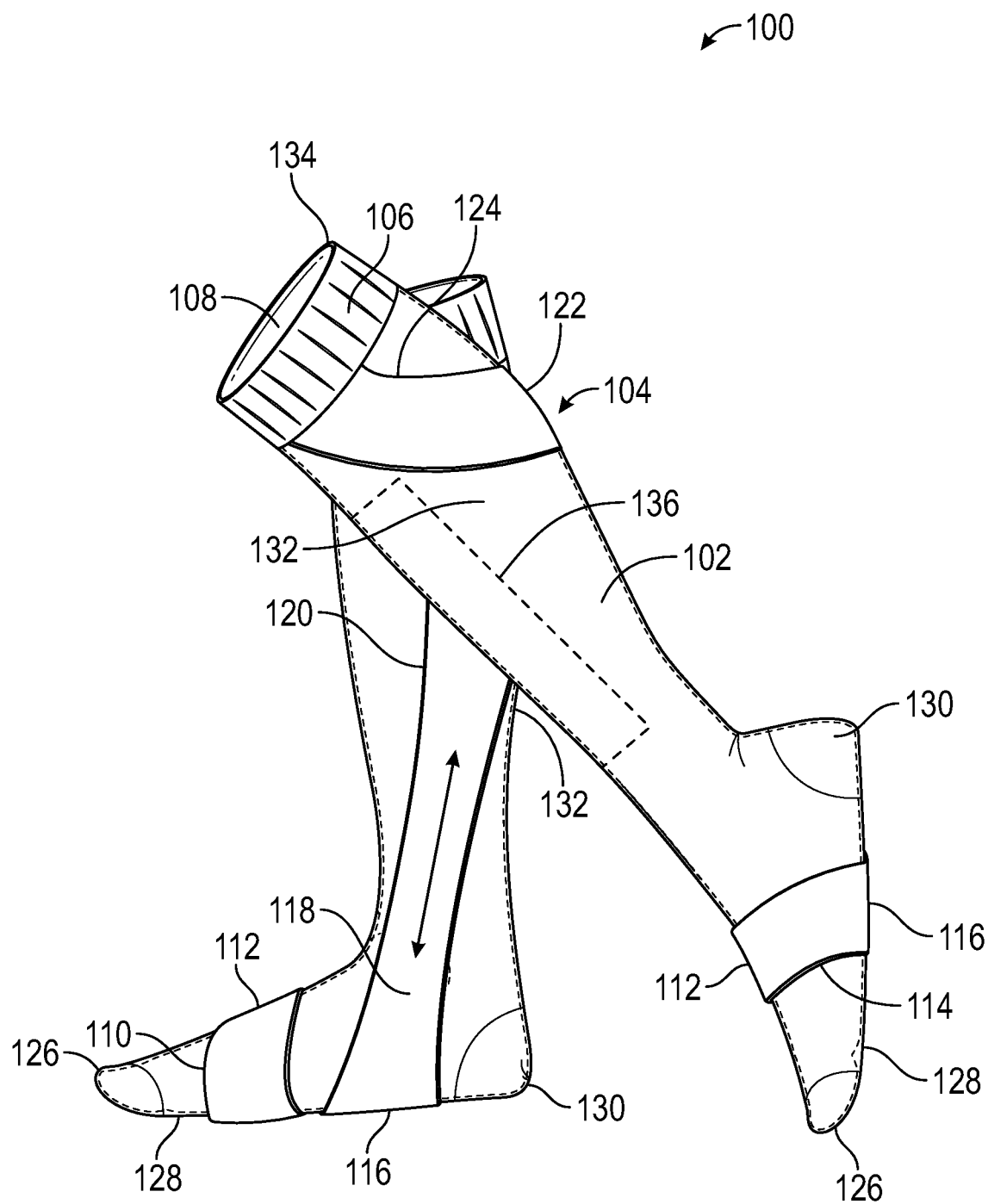
FIG. 2 is a side view of an exemplary dynamic sock according to the present disclosure, the dynamic sock including a propulsion band that provides anatomical assistance to propulsive tendons of the foot and lower leg.

With reference to FIG. 2, a side view of a first embodiment of an exemplary dynamic compression/propulsion sock 100 (hereinafter "sock 100") of the present disclosure is provided. FIG. 2 shows the sock 100 as worn on both the right and left legs of the user. It should be understood that the sock 100 for the right leg is a mirror image of the sock 100 for the left leg. The sock 100 is intended to provide propulsion to the user, thereby improving performance of the user during a normal gait cycle.

Although the sock 100 is intended primarily for performance improvement, it may also be of assistance from a medical perspective. Although the primary purpose of the proposed sock is joint-control, whether for performance or joint alignment, one must also consider the benefits of the described invention for certain medical benefits. Compression socks for medical uses are designed to promote and assist blood flow, prevent the formation of clots, and reduce pain. They are generally used to treat diseases in the veins of the lower leg. They may be used to treat edema, venous insufficiency, deep vein thrombosis (DVT), varicose veins, lymphedema, phlebitis or treatment of vein compression due to pregnancy among other diseases. The wearing of any medical grade compression socks must be prescribed and supervised by a medical professional. Iterations of the described invention for medical purposes would generally require higher compression. Standard compression levels of socks are as follows: about 8-15 mmHg for light compression, about 15-20 mmHg for moderate compression, about 20-30 mmHg for Class I firm compression, about 30-40 mmHg for Class II medical grade compression, and about 40-50 mmHg for Class III highest grade compression. Although medical utilization of the device is not the primary aim, the described dynamic socks can utilize the higher compressions in order to achieve therapeutic benefits in certain cases.

The sock 100 includes a main body section 102 (e.g., a primary or lower layer) that covers the entire surface area of the leg intended to be covered by the sock 102. For example, the sock 100 of FIG. 2 is intended to cover the entire foot and lower leg to the top of the calf, and the main body section 102 covers this entire area. The main body section 102 is fabricated from a low compression material (e.g., Spandex, a woven material, or the like) having a compression of about 8-15 mmHg, thereby providing a generally constant compression to the leg of the user.

The sock 100 includes one or more propulsion bands 104 (e.g., a secondary or outer layer) that provide anatomical assistance to the propulsive tendons of the foot and lower leg. During fabrication of the sock 100, the main body section 102 can be fabricated first prior to attachment and/or integration of the propulsion bands 104 with the sock 102. In some embodiments, each sock 100 can include a single, elongated propulsion band 104 that is selectively positioned or wrapped around the main body section 102 to provide the intended anatomical assistance to the propulsive tendons. In some embodiments, an elastic top cuff 106 can be sewed or connected to the top perimeter of the main body section 102 to reduce slippage of the sock 100 down the wearer's leg while running, walking, jumping, or the like. In some embodiments, a dot silicone elastic tape 108 or similar no-slip material can be sewn into the top cuff 106 of the sock 100 to further assist in slippage reduction of the sock 100 during use. For example, the elastic tape 108 can be positioned on the inner surface of the top cuff 106 to provide a friction fit against the leg of the user. In some embodiments, the sock 100 can include a pocket 136 formed in the main body section 136 at a location corresponding with the shin. The pocket 136 is configured and dimensioned to removably receive a shin/leg guard.

The band 104 includes a power or propulsion band. The power/propulsion band 104 defines a width of, but not limited to, about, e.g., 1-3 inches inclusive, 1-2.5 inches inclusive, 1-2 inches inclusive, 1-1.5 inches inclusive, 1-1.25 inches inclusive, 1.25-3 inches inclusive, 1.5-3 inches inclusive, 2-3 inches inclusive, 2.5-3 inches inclusive, 1 inch, 1.25 inches, 1.5 inches, 1.75 inches, 2 inches, 2.5 inches, 3 inches, or the like. However, it should be understood that depending on the applications/use of the sock 100, the width of the propulsion band 104 can be customized to ensure the desired and proper support and assistance is provided. For example, greater support can be achieved with a propulsion band 104 having a greater width, while lower support can be achieved with a propulsion band 104 having a smaller width.

In some embodiments, the main body section 102 of the sock 100 can be formed in a basket weave pattern with a relatively high weave density in the propulsion band area and a relatively low weave density in other areas. For example, the main body section 102 can be formed from a low weave density, thereby providing a low level of compression, while the propulsion band 104 can be formed from a high weave density to provide greater compression/tension. Generally, in textile manufacturing, the fabric density is determined by the thread count of warp and weft (horizontal and vertical) aligned threads per square inch or per square centimeter. The higher the thread count, the higher the weave density. In addition, the Jacquard technique stitching of the tension bands can include elastic thread that can be composed of a higher percentage of rubber for increased resistance in the band area. In some embodiments, the material blend can include, but is not limited to, a combination of polyester and rubber. In some embodiments, the main body section 102 can be fabricated from thread having a low compression/tension force, and the propulsion band 104 can be sewn into and/or integrated with the main body section 102 in the desired sections using a higher compression/tension elastic thread to provide the desired tension forces. In some embodiments, a mesh weave pattern with an elastic thread that has increased tension can be utilized in one or both sections. In some embodiments, the propulsion band 104 can be fabricated from an elastic material, and can be coupled to the outer surface of the main body section 102 using, e.g., heat welding, adhesive, sewing, or the like. In some embodiments, the propulsion band 104 can be fabricated as a substantially continuous, single band that can be wrapped around and attached to the outer surface of the main body section 102. In some embodiments, the band 104 can be fabricated as two or more continuous bands that can be wrapped around and attached to the outer surface of the main body section 102. In some embodiments, the propulsion band 104 can be selectively integrated and/or sewn into the material of the main body section 102.

The band path for the bands described herein refer to anatomical positions when the socks are worn by the user to clearly identify the different types of band paths and their respective effect on the user. As depicted in FIG. 2, the power/propulsion band 104 can originate at or near the superior aspect of the first metatarsal (section 110, flexor halluces longus), extends laterally and superior to the fifth metatarsal (section 112), wraps inferiorly and proximal to the fifth metatarsal (section 114, flexor digitorum longus), extends medially and posteriorly under the arch of the foot (section 116, plantar fascia), traverses again superiorly (tibialis anterior) and posteriorly toward the medial malleolus (section 118, tibialis posterior), at which point the band 104 traverses superiorly towards the upper part of the calf (section 120), wraps around the lateral gastrocnemius (section 122), and terminates at the lateral aspect of the calf (section 124, peroneal tendon). In some embodiments, the band 104 can split into a medial and lateral branch and terminate at the anterior aspect of the shin, medially and laterally (see, e.g., V-shaped split in FIGS. 3A-3B). The configuration, positioning or pathway of the band 104 is specifically selected to provide assistance to particular tendons of the user by storing potential energy for propulsion in specific areas of the sock 100. The cuff 106 of the sock 100 (formed at the upper perimeter edge/region of the sock 100) can be fabricated from the same material as the propulsion bands 104 (with the same or different level of elasticity), although it may be fabricated from a different material. The material of the main body section 102 therefore covers the entire foot and lower leg (up to the knee) of the user, including the toe 126, forefoot 128, heel 130, and calf 132 up to the upper perimeter edge 134 of the sock 100, and the propulsion band 104 selectively wraps around the lower leg of the user to provide the necessary propulsive assistance.

The configuration of the sock 100 exerts a plantarflexion and inversion moment on the metatarsals in order to "load" them as they extend into dorsiflexion. The band 104 pushes down on the superior aspect of the five metatarsals while at the same time pulling superiorly on the arch while the foot is unweighted. During weight-bearing, the forefoot 128 dorsiflexes and everts in heel-off, in order to absorb and store potential energy in preparation for toe-off. The sock 100 assists the forefoot 128 in absorbing energy in dorsiflexion by using the lever formed by the medial power band (sections 118, 120) extending down the medial leg and under the arch (section 116), thereby using the arch as a fulcrum to plantarflex the foot. In particular, during weight bearing, energy is loaded as the forefoot 128 dorsiflexes and the heel leaves the ground in preparation for toe off during which the stored energy is released at toe off. The sock 100 therefore assists the forefoot 128 in absorbing and storing energy in dorsiflexion by using the lever formed by the medial power band 104 extending down the medial leg under the arch, thereby using the arch as a fulcrum to plantarflex and invert the foot, providing efficient propulsion. Use of the sock 100 can result in the tibia being used as a fulcrum, thereby spreading the load out over a greater surface area during walking, running, jumping, or a similar activity.

Figure 3A:
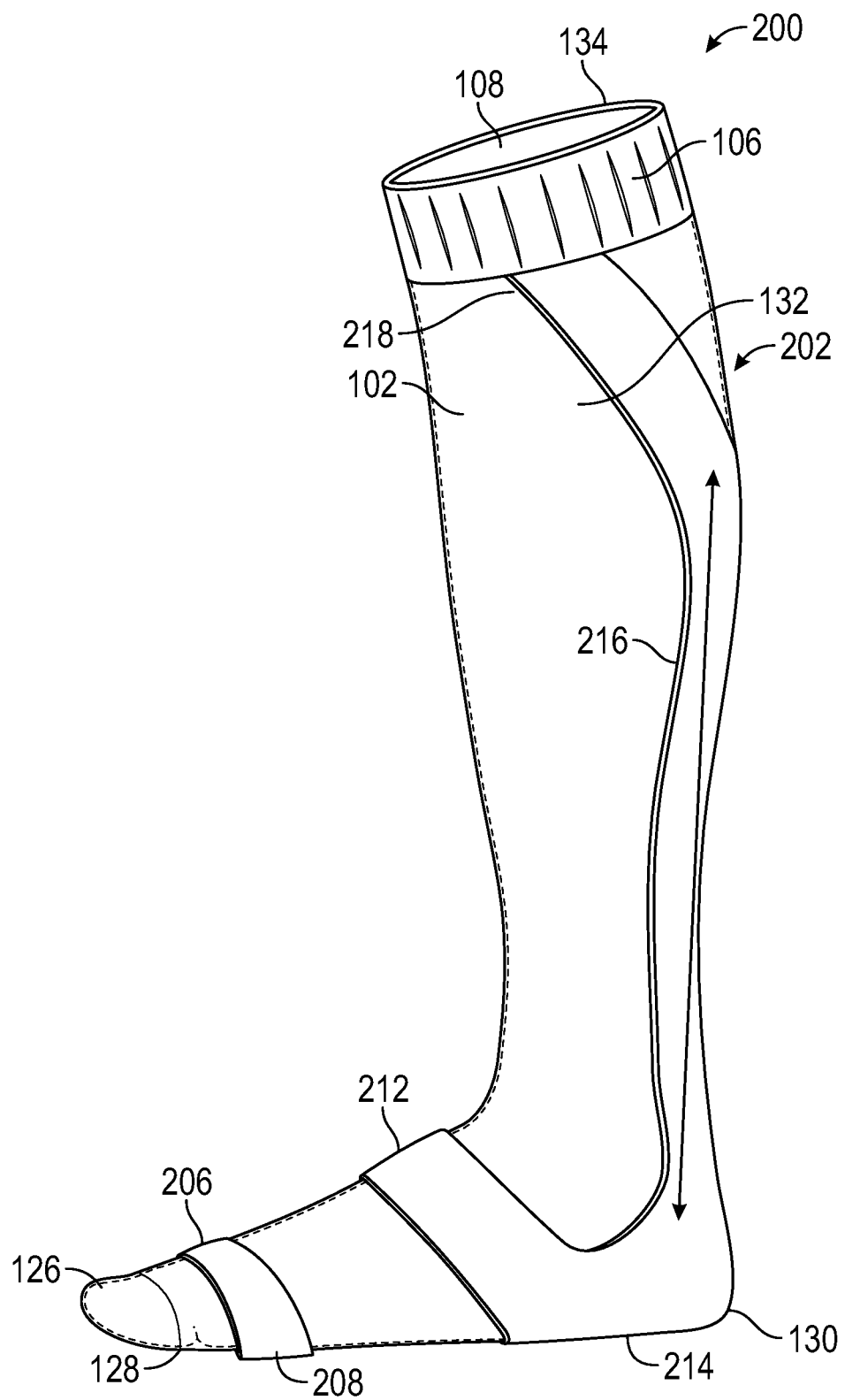
FIG. 3A is an outside foot view and FIG. 3B is an inside foot view of an exemplary dynamic sock according to the present disclosure, the dynamic sock including a propulsion band design that exerts a plantarflexion pressure on the metatarsals.
Figure 3B:
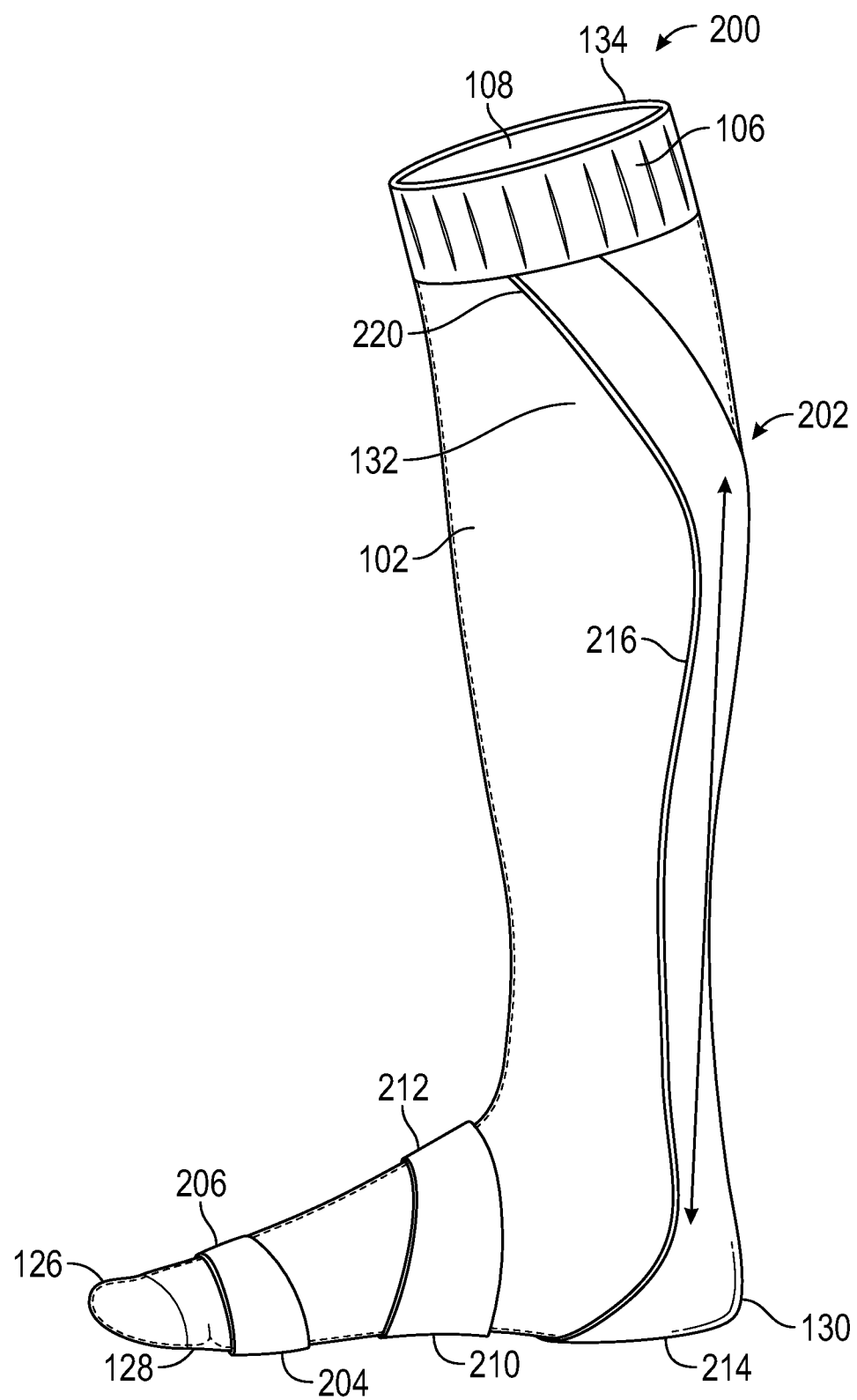

With reference to FIGS. 3A-3B, side views of a second embodiment of an exemplary dynamic compression/propulsion sock 200 (hereinafter "sock 200") of the present disclosure are provided. In particular, FIG. 3A shows the sock 200 as viewed from the outside of the foot, and FIG. 3B shows the sock 200 as viewed from the inside of the foot. The sock 200 can be substantially the same in structure and function to the sock 100, except for the distinctions noted herein. In particular, the sock 200 includes the same main body section 102 and a propulsion/power band 202. However, the path or positioning of the propulsion band 202 relative to the main body section 102 is different from the sock 100.

The band 202 design is configured to exert a plantarflexion pressure on the metatarsals. With respect to the band path, the propulsion band 202 originates superior to the first metatarsal (section 204, flexor hallucis longus), traverses laterally (section 206) and posteriorly to the fifth metatarsal (section 208), wraps inferiorly underneath just proximal to the fifth metatarsal (flexor digitorum longus), and then posteriorly and medially under the arch (section 210, plantar fascia). The propulsion band 202 then proceeds superiorly and posteriorly around the instep (section 212, flexor retinaculum), across and inferior to the lateral malleolus (peroneal tendon), inferiorly under the heel (section 214), and finally track superiorly up the posterior aspect of the calf (section 216, Achilles' tendon). In some embodiments, the posterior band 202 can extend substantially vertically as a single band 202 to the cuff 106. In some embodiments, the band 202 can split into a substantially V-shaped section at or near the top of the calf with portions 218, 220 proceeding medially and laterally, respectively, terminating at the anterior or lateral aspect of the cuff 106. The V-shaped configuration can be used to increase the grip that the sock 200 has on the lower leg by distributing the force downward. In a dynamic closed chain environment, the effect is magnified due to the lever the tibia and fibula exerts on the arch as those bones pass over the midfoot, thereby pulling superiorly on the arch and heel, pulling the forefoot into plantarflexion. The maximally plantarflexed forefoot can store a significant amount of energy in dorsiflexion in preparation for maximum energy return in subsequent plantarflexion. The combination of opposing levers formed by the band 202, upward on the calf, arch and heel and downward on the metatarsals (e.g., $1^{st}$ and $5^{th}$ metatarsals), stores a powerful tensile force in dorsiflexion which is released in plantarflexion. The band 202 must have force equilibrium to work effectively. In particular, the band 202 must exert substantially equal and opposite forces up and down on the foot and leg in order to prevent the sock 200 from pulling down the back of the leg and to control the forefoot. The sock 200 therefore pulls up on the back of the leg, pushes down on the instep of the foot, pulls up on the arch of the foot, and then pushes down on the forefoot.

The further the tibia/fibula progresses past the midfoot in midstance, the more the medial band 202 stretches and the more potential energy is loaded at the arch and the heel, imparting a plantarflexion moment on the forefoot and amplifying the effect of plantarflexion propulsion. The sock 200 therefore returns more energy in an athlete that is crouching down preparing to spring (where the knee is well in front of the foot), than a casual walker. As a result of the long lever arm of the band 202 (owing to the heel wrap), the band 202 exerts more force downward than the band 104 of sock 100. It is because of this that the band 104 configuration of sock 100 may be more appropriate for walkers who require less propulsion, whereas the band 202 configuration of sock 200 may be better for sprinters and runners.

The band 202 pathway exerts plantarflexion pressure on the metatarsals in a static, open chain system (similar to the band 104 pathway of sock 100). However, in a dynamic, closed chain environment, the effect is magnified due to the lever the tibia/fibula exerts on the arch as it passes over the midfoot, thereby pulling superiorly on the arch and pulling the forefoot into plantarflexion. The maximally plantarflexed forefoot can store a significant amount of energy in dorsiflexion in preparation for maximum energy release in plantarflexion.

Figure 4:
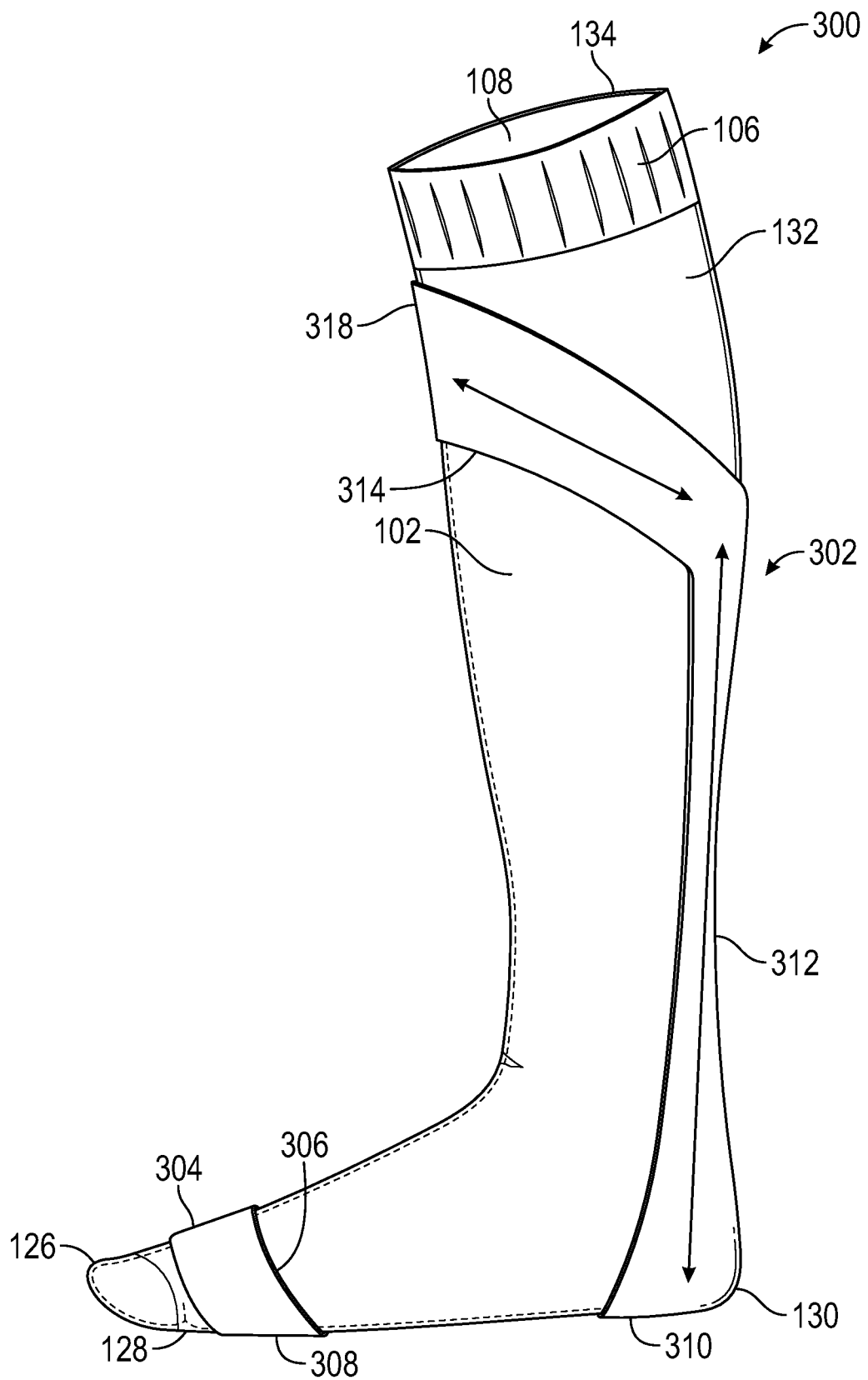
FIG. 4 is a side view of an exemplary dynamic sock according to the present disclosure, the dynamic sock including a removable or semi-removable propulsion band.
Figure 5:
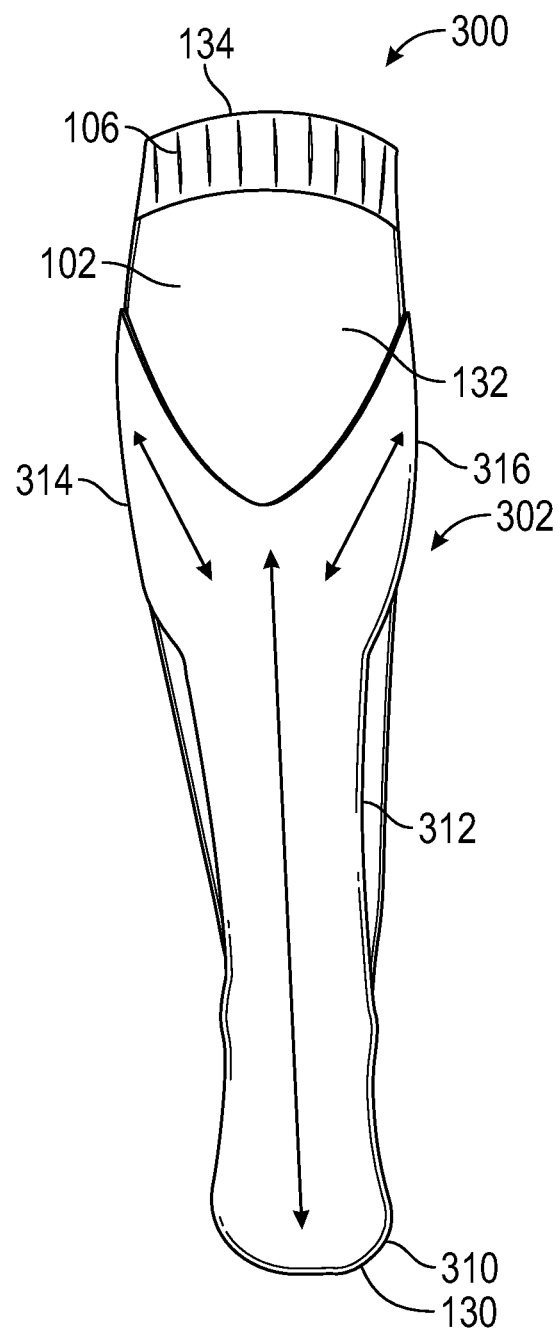
FIG. 5 is a rear view of an exemplary dynamic sock of FIG. 4.

With reference to FIGS. 4 and 5, side and rear views of a third embodiment of an exemplary dynamic compression/propulsion sock 300 (hereinafter "sock 300") of the present disclosure are provided. The sock 300 can be substantially the same in structure and function to the sock 100, 200, except for the distinctions noted herein. In particular, the sock 300 includes the same main body section 102 and a propulsion/power band 302. However, the path or positioning of the propulsion band 302 relative to the main body section 102 is different from the sock 100, 200.

With respect to the band path, the propulsion band 302 originates superior to the metatarsal heads (as in the pathways of the band in sock 100, 200) (section 304), traverses medially and laterally, respectively, posteriorly and inferiorly to the metatarsal heads (only section 306 visible), and wraps inferior to an arch of the foot (plantar fascia and spring ligament) where they join/merge into one wider band (section 308). The wider band 302 then proceeds posteriorly underneath the heel (section 310) and then superiorly up the back of the calf (section 312, Achilles' tendon), where it splits into a V-shaped section at or near the upper part of the calf (tibialis posterior and peroneal tendons) with portions 312, 314. The medial and lateral sections 314, 316 of the band 302 then wrap around the leg, medially and laterally, respectively, and finally join and terminate at the shin just inferior to the patella (section 318, tibialis anterior). The band 302 layout or pathway allows the sock 300 to be bilateral in nature, such that it can be worn on either foot.

Figure 6A:
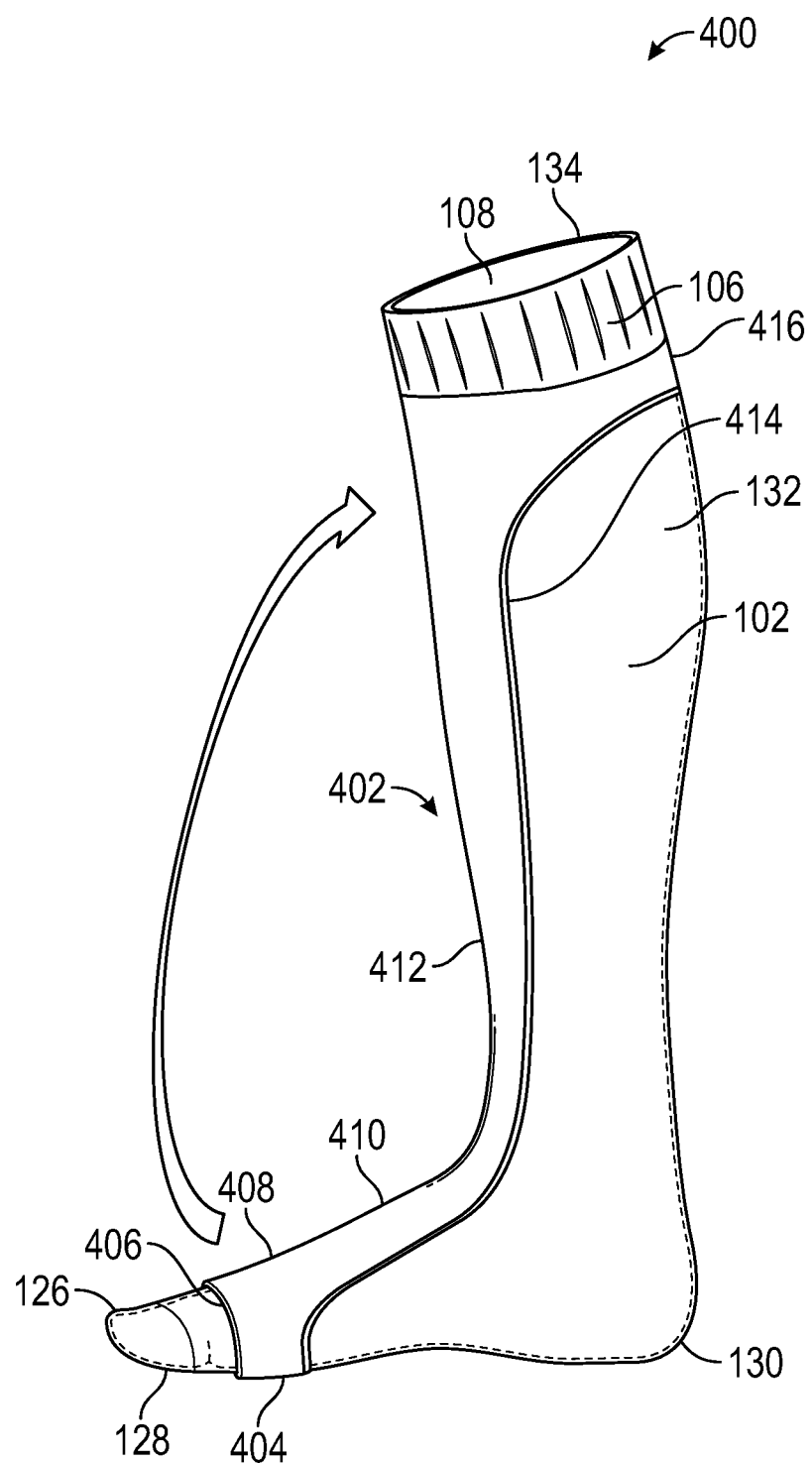
FIG. 6A is a side view and FIG. 6B is a front view of an exemplary dynamic sock according to the present disclosure, the dynamic sock including a tension band configured to maintain a forefoot dorsiflexed.
Figure 6B:
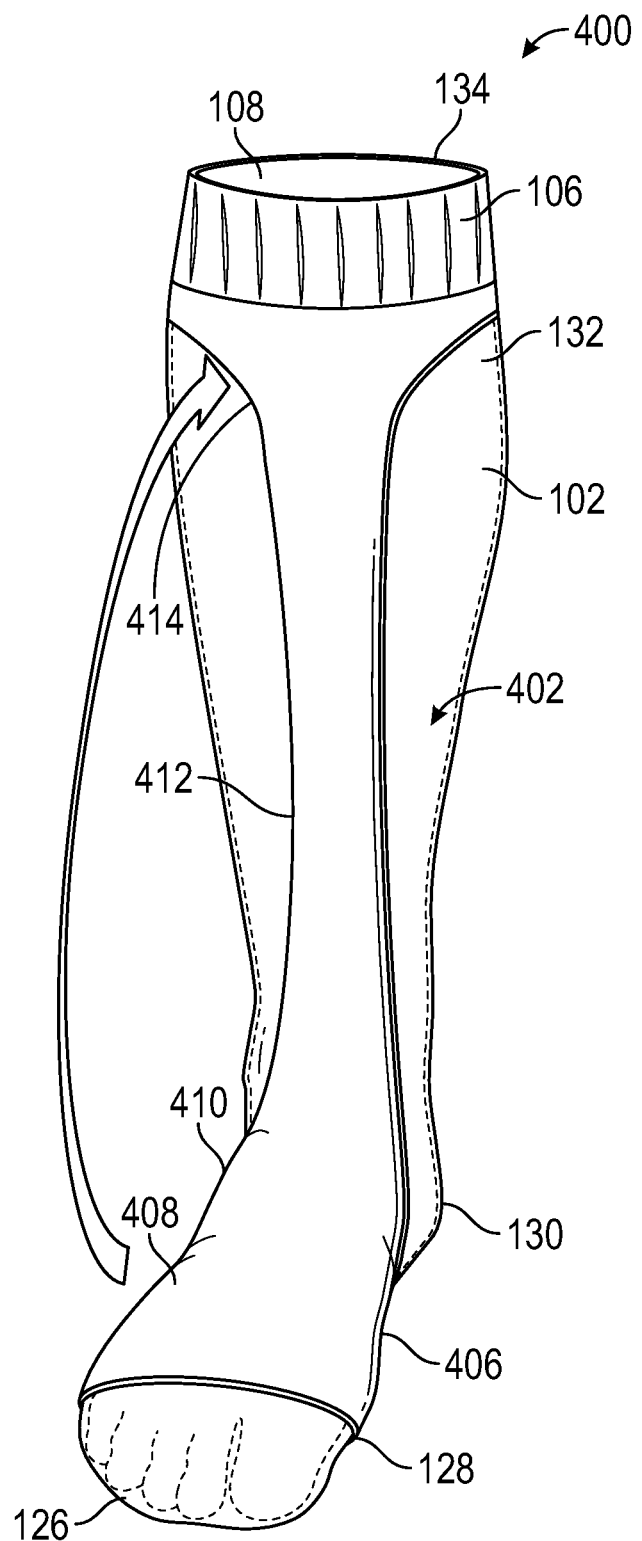

In some embodiments, the unified or merged part of the band 302 can be up to 50% wider than the segregated or individual sections of the band 302, although depending on the different iterations and band configurations, this ratio may vary. The band 302 widths and lengths can be solely determined by the different sock sizes as well as the different methods of joint control. For example, in FIG. 2, the band 104 throughout the entire sock 100 is generally the same width since the band 104 is acting on a larger cross section of the foot and leg. Conversely, in FIGS. 3A and 3B, the proposed bands 202 are narrower in the forefoot, slightly wider in the instep and wider still at the rear of the heel, ankle, calf before splitting into narrower segregated bands 202 at the shin. Further, in FIG. 4, the proposed band 302 can be narrower in the metatarsals, and gradually gets wider as it traverses under the plantar aspect of the foot, heel and lower calf before it separates into two narrow bands. In FIGS. 6A and 6B, the bands 402 underneath the metatarsals joint into a band 402 that covers the entire forefoot for maximum leverage to assist in pulling the forefoot up. Since there are no accepted standards in sock manufacturing regarding the ratios between sock sizes, the actual dimensional differences between the socks and by extension the sock bands, can vary greatly. The proposed invention could be available in standard sock sizes as follows; extra small, small, medium, large, extra-large, and extra-extra-large (XXL), but shall not be limited to such sizes. The width of the band is generally consistent throughout the pathway although the width at the heel, as it traverses up the Achilles' tendon, may be slightly wider to accommodate the full width of the heel in order to wrap around medial and lateral side and cup the entire rear portion of the foot for maximum heel control. In band configurations that traverse up the posterior aspect of the leg, e.g., FIGS. 3A, 3B, 4 and 5, the band can split about 60% of the way up the leg, although this may vary substantially depending on application.

In some embodiments, the propulsion band 302 may not be stitched or attached to the sock 300 over the entire path of the band 302, but instead can be attached only at certain segments of the band 302. For example, the outer surface of the main body section 102 can include securement features capable of releasably engaging with an inner surface of the band 302, allow for reconfiguration and/or optimization of the pathway of the band 302 depending on the specific needs of the user. In some embodiments, the band 302 can be a removable or semi-removable band 302 that can attach, e.g., with a VELCRO® closure, at varying points on the sock 300. In such configuration, the tension of the band 302 can be adjusted by the user depending upon how tightly the strap is cinched. In some embodiments, alternative embodiments of the socks can use a similar detachable/reconfigurable design. In some embodiments, the sock 300 can use the heel as a fulcrum. Such configuration amplifies energy storage at the dorsiflexion ankle, thereby increasing propulsion at plantarflexion.

With reference to FIGS. 6A-6B, side and front views of a fourth embodiment of an exemplary dynamic compression/tension sock 400 (hereinafter "sock 400") of the present disclosure are provided. The sock 400 can be substantially the same in structure and function to the sock 100, 200, 300, except for the distinctions noted herein. In particular, the sock 400 includes the same main body section 102. However, rather than a propulsion band, the sock 400 includes a tension band 402. The tension band 402 can be fabricated of a substantially similar material as the propulsion bands discussed herein, while providing a different tensioning force for assistance with a medical condition(s) of the user. In some embodiments, the tensioning force provided by the tension band 402 can be substantially equal to the force provided by the propulsion bands discussed herein. In some embodiments, the tensioning force provided by the tension band 402 can be greater than the force provided by the propulsion bands, generated by an increase in thread count and materials that may be necessary to accomplish increased tension. The band 402 configuration can be adapted to be used for, inter alia, medical conditions including, but not limited to, foot drop, anterior tibialis weakness, stroke, or other neurological conditions that may impair gait. By arranging the band 402 such that the forefoot is dorsiflexed instead of plantarflexed, the sock 400 can apply more tensile force to the dorsum in order to assist the anterior tibialis tendon in helping the foot to clear the ground during gait. Frequently, patients with these conditions experience weakness in the anterior tibial tendon causing the forefoot to drop and, therefore, not clear the ground as they bring the leg forward. Such condition can result in tripping.

The traditional treatment in patients with these conditions is generally an ankle/foot orthotic (AFO) made of a polypropylene or carbon fiber material designed to keep the forefoot dorsiflexed such that the patient's foot can clear the ground while walking. One problem with the traditional ankle/foot orthoses is that once a patient accommodates to the orthosis, it is nearly impossible to wean them from using it. The sock 400 of FIGS. 6A-6B provides an improvement for assistance with such conditions. In addition, prices for AFO braces are normally in the $1,000-$1,500 range and the braces can be cumbersome, usually forcing the patient to purchase footwear that is too large for them in order to accommodate the brace which can make the tripping risk greater.

With the sock 400, in an open chain, the foot is kept in dorsiflexion tension by having the compressive bands 402 work in an eccentric rather than a concentric fashion. With respect to the band path, the band 402 runs underneath the metatarsal heads to support them, runs up the dorsum of the foot, and then extends up the anterior aspect of the leg. In particular, the tension band 402 originates under the metatarsal heads (section 404), proceeds superiorly, medially and laterally (section 406), then joins over the metatarsals (section 408). The band 402 then runs up the dorsum (instep) of the foot (section 410, extensor hallucis longus and extensor digitorum longus), proceeding superiorly over the front of the ankle (retinaculum) and then up over the shin (section 412, tibialis anterior), where it again splits just inferior to the kneecap (section 414), then proceeds medially and laterally around the calf and finally joining at the anterior of the shin or the posterior aspect of the upper calf (section 416). The band 402 thereby forms a termination section that extends completely around the main body section 102 adjacent to the cuff 106. This way, during gait, the anterior tibialis tendon, a main dorsiflexor of the foot, is assisted. In particular, the band 402 extending under the metatarsal heads and then up the shin supports the metatarsal heads, and then extends over the dorsum of the foot and up the shin, exerting a pull up force on the metatarsals to assist the patient in raising their forefoot.

Instead of using the arch or heel as a fulcrum, the sock 400 can advantageously have the bands 402 run underneath the metatarsal heads medially and laterally (crossing in a substantially X-shaped configuration) over the instep to keep the foot in a dorsiflexed position, and then the individual bands can join into one wider band 402 over the dorsum of the foot. The more acute the angle of the foot to the leg, the more dorsiflexion assistance to the patient.

The power bands 402 associated with the present disclosure are strategically located to assist the anatomical lever system in the foot, ankle and lower leg, making the dynamic sock 400 an anatomical extension of the human body.

Regardless of the band 402 configuration, the disclosed dynamic use of the natural motion, torque and momentum of the human body transforms the dynamic garment into an anatomical assist by enhancing the normal lever system of the body and exerting an exoskeletal effect on the foot and ankle to more efficiently store potential energy and release kinetic energy to perform a given work. In the embodiment of FIGS. 6A-6B, joint assist is made possible by the disclosed configuration of the unibands (e.g., band 402). Unibands have the unique property of being very elastic in one direction and very resistant in another to accomplish a given work. In FIGS. 6A-6B, the high compression weave uniband material is illustrated in black while the low compression weave material is illustrated in white. In this way, the garment that they are part of can easily be put on and comfortable to wear, but simultaneously be resistant in a different plane in order to store and release energy in the desired direction.

In the embodiment of FIGS. 6A-6B, instead of having the properties of a compression sock material which applies pressure fairly consistently against the leg in one plane, the described propulsion sock 400 with uniband technology applies tensile force in the band 402 area and medium compression against the leg at the main body portion 102. These bands 402 are highly resistant when stretching against themselves. This is accomplished through a unique weave design with fibers biased in multiple directions to provide elasticity. In some embodiments, the unique weave design or method can be (but is not limited to), e.g., the Jacquard weaving technique, where precision computerized looms knit a single or double jacquard pattern with varying composition threads in order to achieve the proper tension in the band 402.

The socks of the disclosed configurations of FIGS. 2-6B have band configurations that typically terminate under the knee into a cuff 106 designed to keep the sock from pulling or sliding down the leg. If the sock were permitted to pull down the leg, the sock's leverage and thereby its effectiveness would be reduced. The power bands are strategically located to assist the anatomical lever system in the foot, ankle and lower leg, making the dynamic sock an anatomical extension of the human body.

Regardless of band configuration, this dynamic use of the natural motion, torque and momentum of the human body transforms the dynamic sock into an anatomical "assist" by enhancing the normal lever system of the human body and exerting an exoskeletal effect on the foot and ankle to more efficiently store potential energy and release kinetic energy to perform given work. Normal compression socks apply pressure inward toward the leg. Instead of applying pressure against the leg, the disclosed sock 400 applies tensile stress against itself by use of stretch bands.

Using a different band configuration than the previously discussed socks, the described dynamic propulsion sock 400 can also be used for drop-foot, anterior tibialis weakness, stroke or other non-rigid deformities. By arranging the bands 402 such that the forefoot is dorsiflexed instead of plantarflexed, the sock 400 can apply more tensile force to the dorsum of the foot in order to assist the anterior tibialis tendon in helping the foot clear the ground during gait. Many patients that experience foot drop develop a "steppage" or "circumduction gait" where they make compensatory accommodations to allow the foot to clear the ground by raising the entire leg and hip with each step, so as not to trip and fall.

In this iteration, the sock 400 would be woven in an acute angle design such that the ankle joint is guided into dorsiflexion with added compression between the anterior arch and the superior aspect of the malleoli. The intent of the configuration of the sock 400 is not propulsion, but rather control and assist of a weakened muscle or tendon. Patients with these conditions experience weakness in the peroneal, and to a lesser extent the anterior tibial tendon, causing their forefoot to drop and thus drag on the ground as they bring the leg forward which may cause tripping. Patients with foot drop may develop a steppage gait whereby they must raise the hip in order to have the foot clear the ground.

In each of the sock designs that are intended to increase propulsion (e.g., socks 100, 200, 300), the sock can have a substantially tube sock design (straight design) with increased compression at the arch/heel ankle such that the ankle/foot complex can be guided into plantarflexion in order to increase the amount of potential energy stored during dorsiflexion to return that energy at plantarflexion. The sock without any addition of propulsion bands would still have a material effect on the position and function of the foot.

In the case of the dropfoot assist sock (e.g., sock 400), the design can be made with exactly the opposite intention to the propulsion sock, in that the sock would have an acute angle shape in a relaxed state, where the compression of the sock and the shape of the sock would guide the foot into dorsiflexion. In this iteraton, the purpose of the sock would be not concentric assist; it would be eccentric assist and control.

The configuration of the sock 400 can assist the anterior tibialis and peroneal tendon in dorsiflexing the foot in cases where dorsiflexion function by the tendons is insufficient. The dropfoot assist sock can function as a rehab device for those patients whose muscle function is compromised, but who are capable of improvement with moderate exercise. This function separates the dropfoot assist sock from the standard treatment with an AFO, because it maintains the patient's ability to be fully rehabilitated from the condition that's being treated. This is important, because one of the primary disorders that causes dropfoot is transient damage to the superficial peroneal nerve. By assisting with normalizing gait while the nerve recovers, the dropfoot assist sock helps prevent permanent disability in a select group of patients.

In some embodiments, the described propulsion bands can include a higher weave density instead of elastic bands. Such higher weave density is intended to pull/push in the saggital plane. The high compression bands must be offset on the opposing side with very low compression (stretchy) material in order to allow the bands to control the desired joint. As the high compression bands pull the foot into the desired direction, the low compression material on the opposing side must give way in a substantially equal amount in order to allow the higher compression bands to perform their intended function. If the sock was similar compression/tension on all sides, the pull would be the same on both sides and no work would be performed by the sock.

Figure 7:
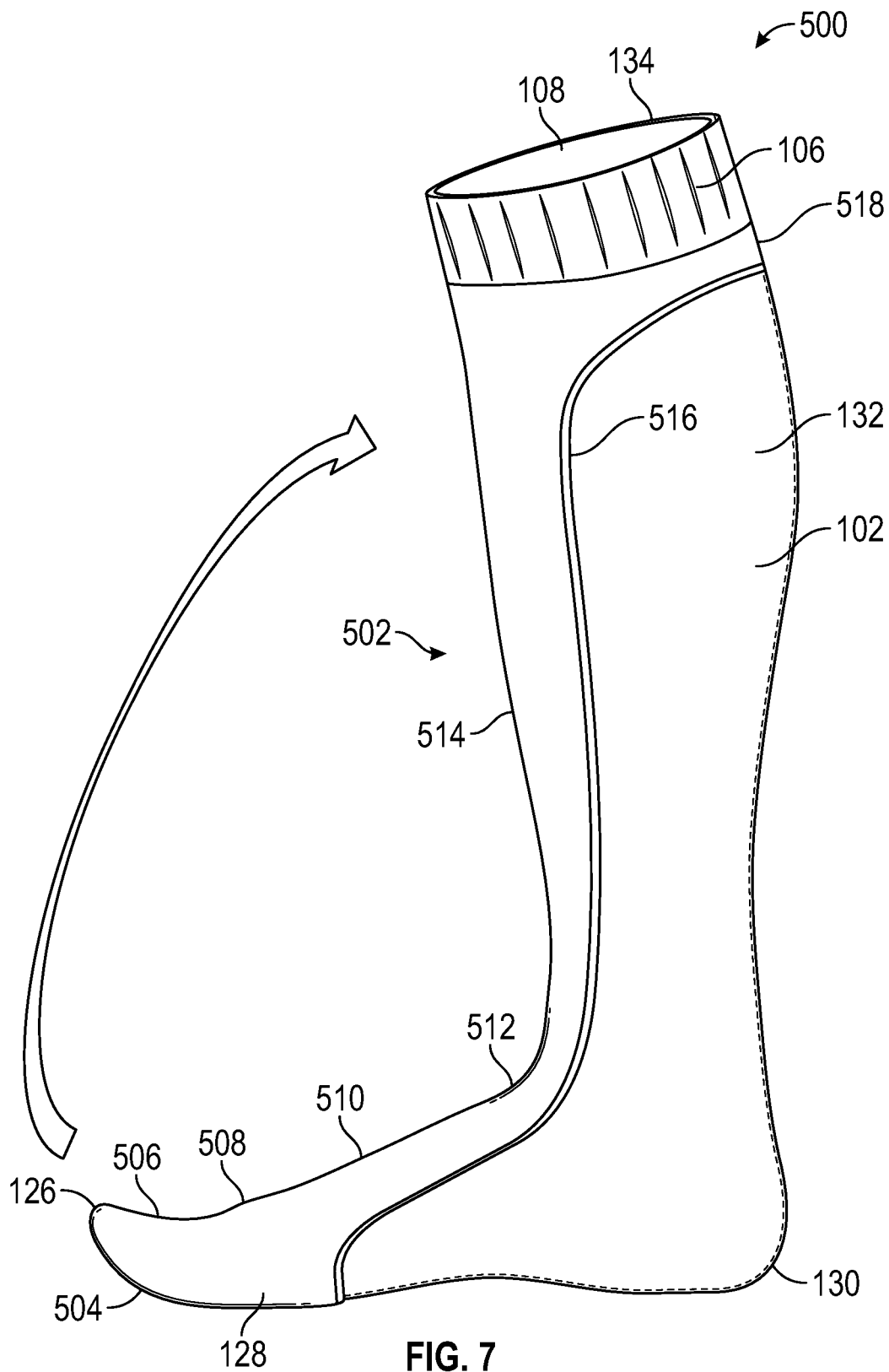
FIG. 7 is a side view of an exemplary dynamic sock according to the present disclosure, the dynamic sock including a tension band configuration for a drop foot assist.
Figure 8:
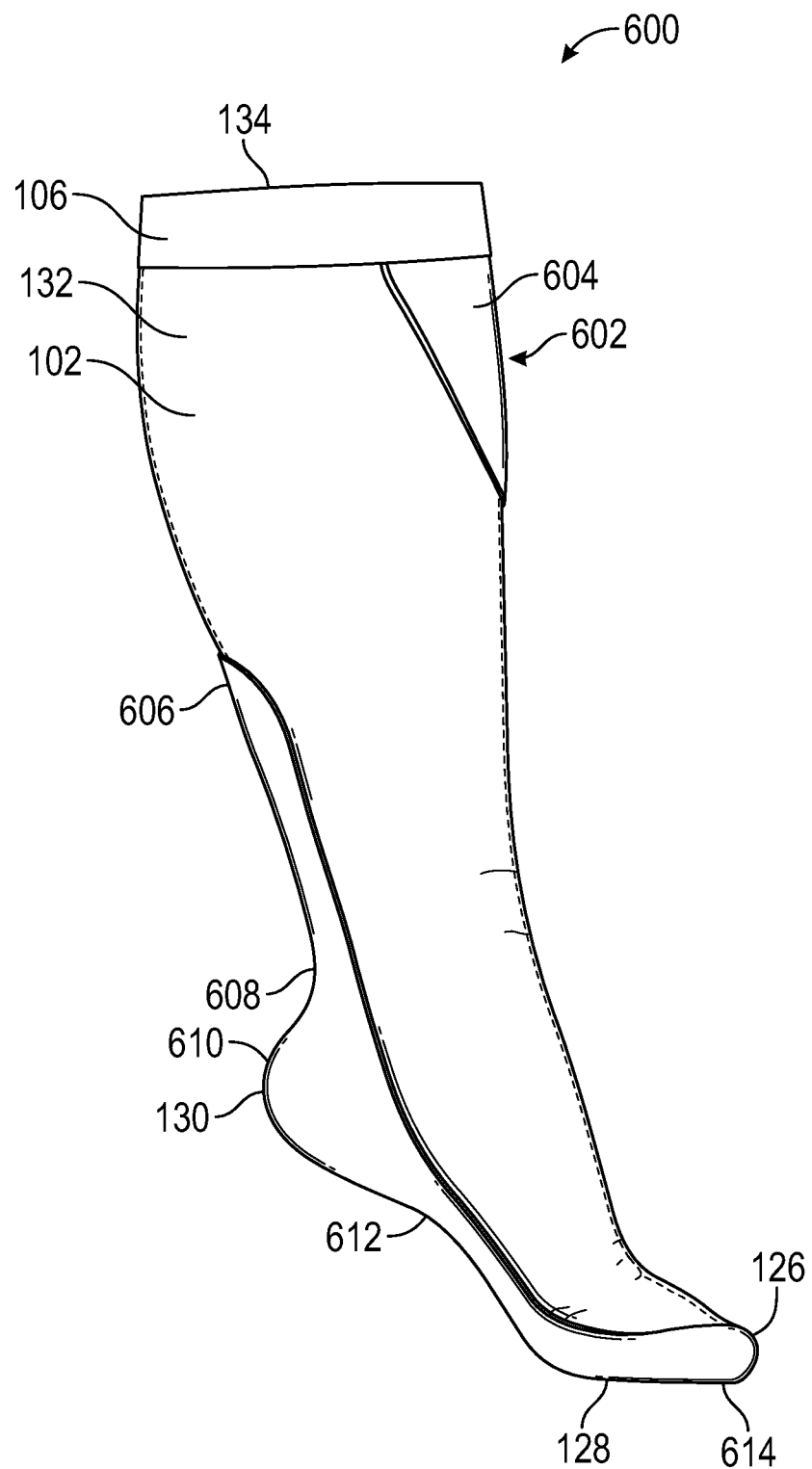
FIG. 8 is an inside left foot view of an exemplary dynamic sock according to the present disclosure, the dynamic sock including a tension band configuration for hallux valgus treatment.
Figure 9:
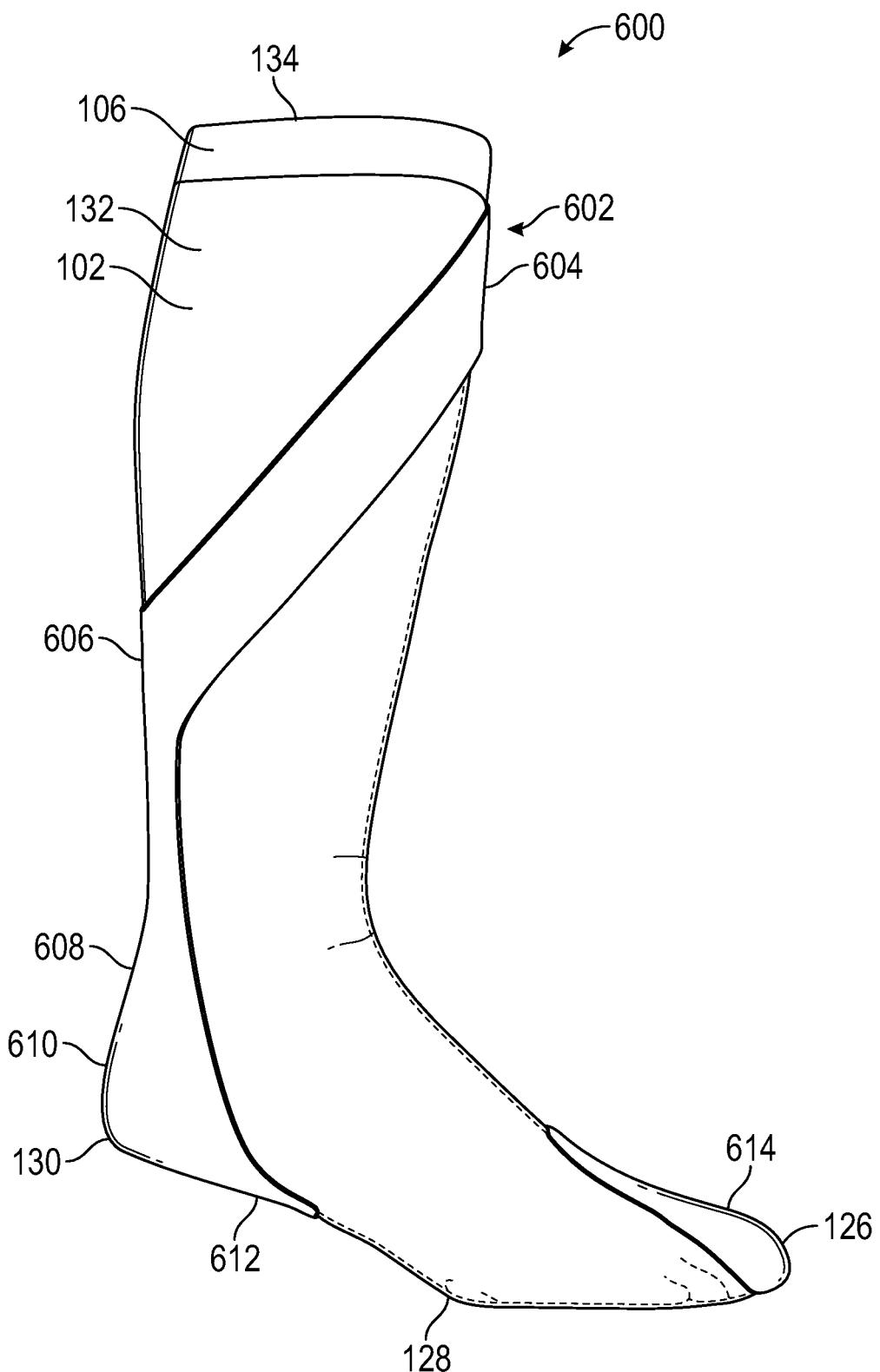
FIG. 9 is an outside right foot view of an exemplary dynamic sock of FIG. 8.
Figure 10:
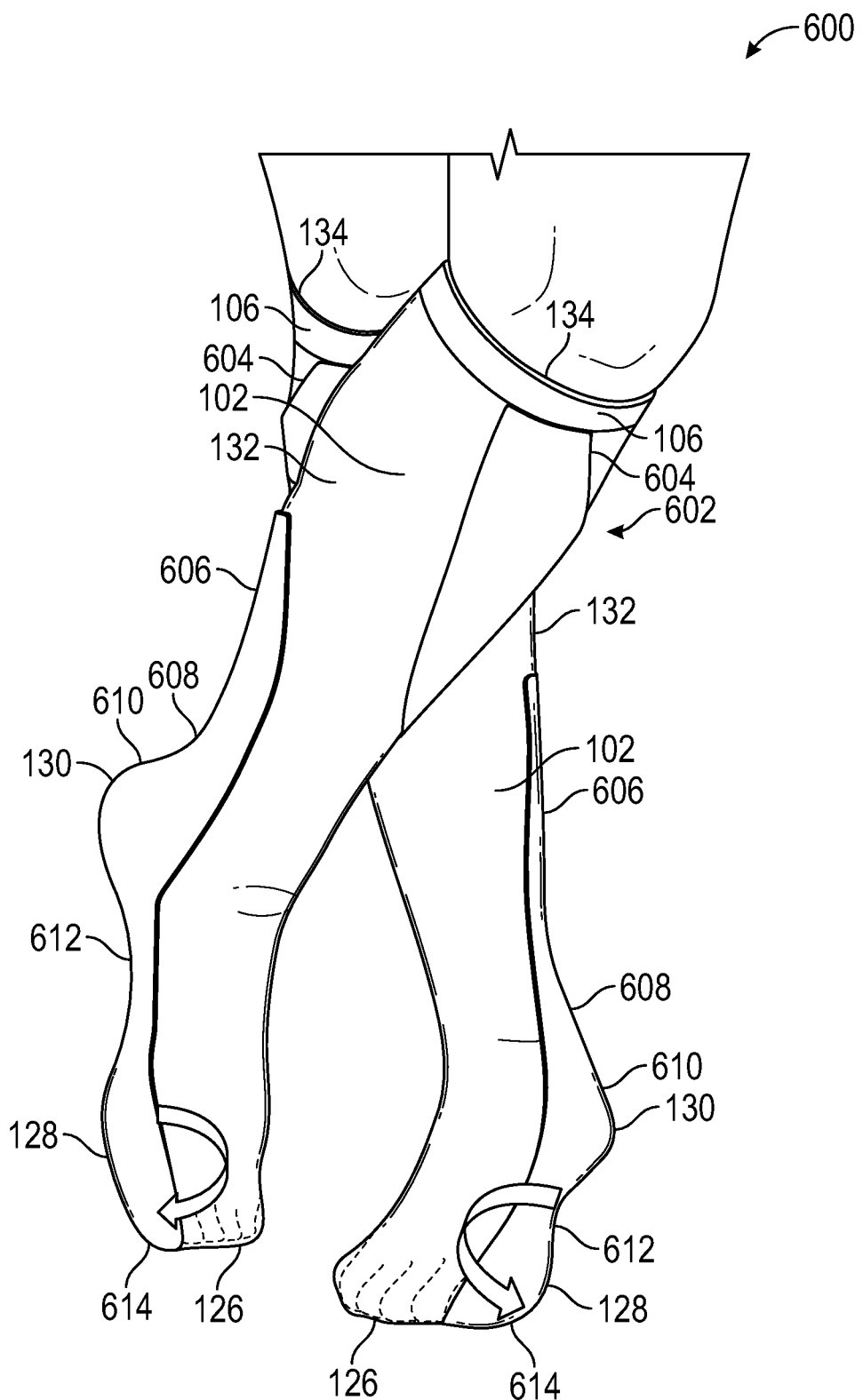
FIG. 10 is a front perspective view of an exemplary dynamic sock of FIG. 8 on both left and right legs.
Figure 11:
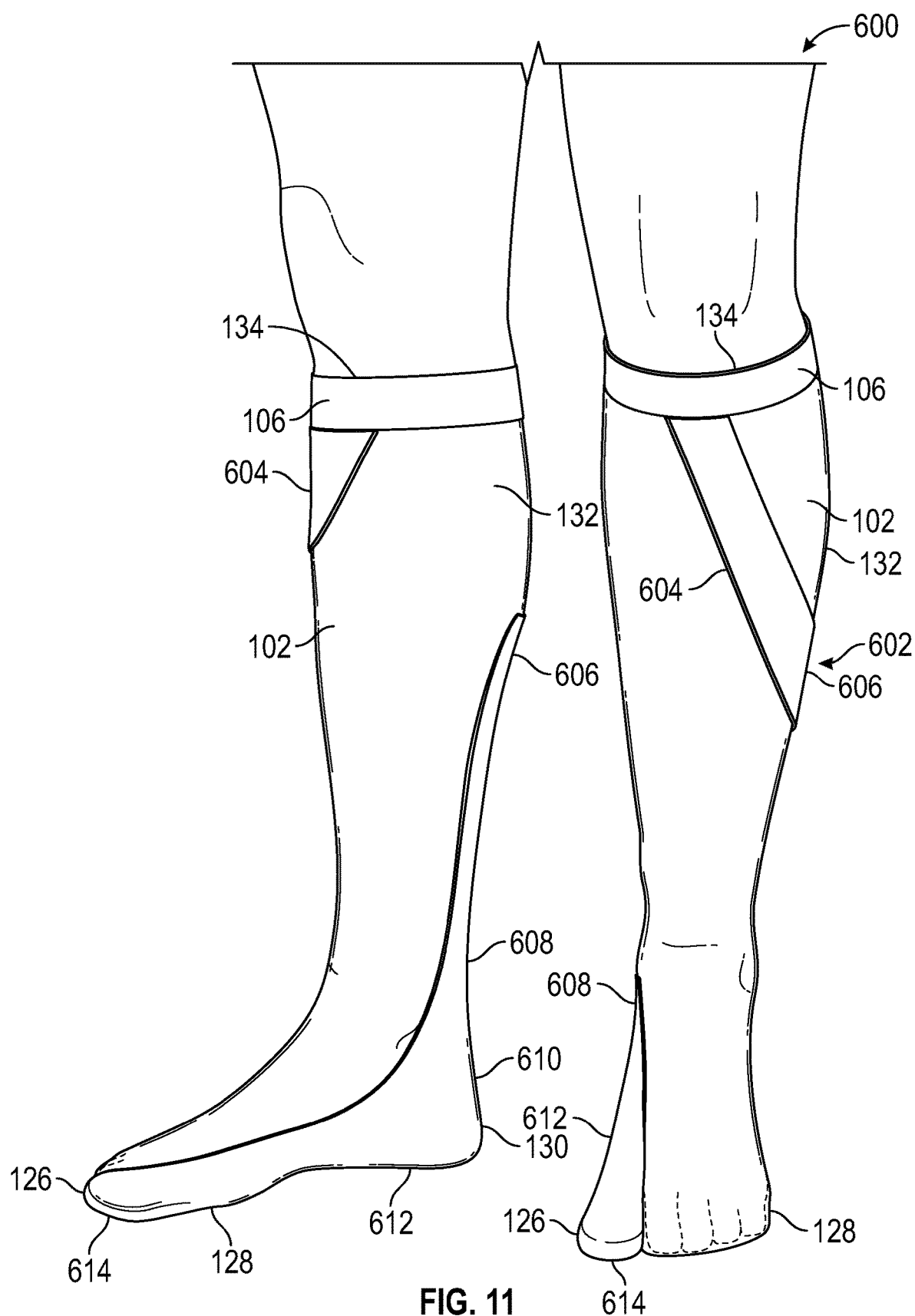
FIG. 11 is a front perspective view of an exemplary dynamic sock of FIG. 8 on both left and right legs.

With reference to FIG. 7, a side view of a fifth embodiment of an exemplary dynamic compression/tension sock 500 (hereinafter "sock 500") of the present disclosure is provided. The sock 500 can be substantially the same in structure and function to the sock 400, except for the distinctions noted herein. In particular the sock 400 includes the same main body section 102 and a tension band 502. The band 402 configuration of FIGS. 6A-6B for drop foot assist can be adjusted or adapted in the pathway of the band 502 to treat plantar fasciitis as a night splint sock or daytime wear sock.

In particular, the band configuration of FIGS. 6A-6B can be altered slightly for individuals that suffer from Plantar Fasciitis. Plantar Fasciitis is a very common foot issue, affecting millions of people annually. It presents as pain upon arising in the morning or after sitting for prolonged periods and then applying weight. This pain is generally caused by the fascia being pulled away from the heel bone when weight is applied. When unweighted, the fascia relaxes and the foot contracts. Then when weight is applied again the pain returns and the cycle continues. Common treatments for Plantar Fasciitis include steroid injections, plasma therapy, ultrasonic tissue repair, NAIDs and orthotics. No matter what the preferred treatment option, addressing Plantar Fasciitis includes stretching the plantar fascia either by a series of exercises, night splints or some combination of both. The night splint is designed to be worn while sleeping, when the foot is unweighted and the fascia is not pulled tight. This stretching routine elongates the Plantar Fasciitis slightly so the tension on the fascia is lessened, thereby easing the pull on the fascia insertion at the anterior aspect of the calcaneous (heel bone). In the embodiment of FIG. 7, the band 502 path can be altered slightly to exert a dorsiflexion "pull" on, not only the ankle, as in the dropfoot configuration (FIGS. 6A-6B), but also the toes.

With respect to the band path, the tension band 502 can originate at the anterior aspect of the shin, proceeds down over the dorsal (top) of the instep, and then terminate underneath the toes. In particular, the tension band 502 can originate under the toes (including the sulcus) (section 504, flexor hallucis and flexor digitorum longus), proceeds superiorly over the top of the toes (section 506, extensor hallucis and extensor digitorum longus), and then extends over the superior aspect of the metatarsals (section 508). The band 502 then extends up the dorsum (instep) of the foot (section 510, tibialis anterior), proceeds superiorly over the front of the ankle (section 512, retinaculum), up over the shin (section 514), anterior to aspect of the tibia, where the band 502 splits just inferior to the kneecap (section 516), and then proceeds medially and laterally around the calf and finally joins at the posterior aspect of the upper calf (section 518). The band 502 thereby forms a termination section that extends completely around the main body section 102 adjacent to the cuff 106. The band 502 configuration can exert a gentle stretching of the plantar fascia while sleeping such that when the individual arises, the Plantar Fascia is looser and does not pull on the heel. In particular, the positioning of the band 502 creates a tension force that pulls up on the foot and the toes to assist with Plantar Fasciitis stretching.

The sock 500 provides practitioners and patients with a conservative, non-invasive option for treating plantar fasciitis, improving patient compliance and providing a complement to other chosen therapies. In some embodiments, the described drop foot assist sock 400 of FIGS. 6A-6B can be fitted with a toe cap fabricated of a firm yet flexible material attached to the sock in a dorsiflexed position to keep the fascia stretched. More clearly, the sock would keep the foot/ankle dorsiflexed at the ankle and the toe cap would keep the toes dorsiflexed. Such toe cap can be affixed by any number of means including but not limited to adhesion, sewing, fusing, Jacquard knitting or other methods.

With reference to FIGS. 8-11, side and front views of a sixth embodiment of an exemplary dynamic compression/tension sock 600 (hereinafter "sock 600") of the present disclosure are provided. The sock 600 can be substantially the same in structure and function to the sock 400, 500, except for the distinction noted herein. In particular, the sock 600 includes the same main body section 102 and a tension and 602.

The band 602 pathway can serve to treat hallux valgus, a condition where the big toe joint begins to dislocate laterally toward the second toe. This condition often presents with a bunion, an exostosis on the medial side of the first metatarsal, which can result in arthritis and/or bone spurs of the big toe, limiting the normal range of dorsiflexion and making walking or running painful. In many cases, because of this lateral displacement of the big toe, the lesser toes may develop a hammer toe condition whereby the toes contract, often making footwear uncomfortable.

The sock 600 can be designed to exert a gentle pull on the great/big toe to guide it back into the proper position, thereby stretching the tendons on the lateral side of the great toe such that the pull laterally would not be as great. The sock 600 can include a tension band 602 that can pull on the medial side of a pocket that the great toe would sit in. The band 602 pathway can be strategically placed such that the tension band 602 originates at the front shin area (front of the tibia) (section 604, tibialis anterior), just inferior to the patella, proceeds laterally and inferiorly around the lateral side of the calf (section 606, peroneals), laterally and inferiorly around the ankle (section 608), then medially around the back of the heel (section 610), inferior to the medial malleolus (tibialis posterior), and then straight forward on the medial side of the foot (section 612), terminating at the distal medial aspect of the big toe (section 614, flexor hallucis longus and flexor digitorum longus). An individual can wear the sock 600 during the day inside of footwear and/or as a night splint while sleeping. The consistent pull on the medial side of the toe can lessen the angle of dislocation, preventing further excursion of the toe laterally and lessen the chance of developing osteoarthritis of the great toe.

Energy Conservation

In general, the socks discussed herein assist healthy muscles and tendons in accomplishing a given amount of work more effectively and more efficiently. In the case of the drop foot assist, plantar fasciitis, or hallux valgus night splint embodiments, the focus is to assist weakened muscles and tendons in accomplishing their functions. As a direct result of assisting the propulsive muscles and tendons of the foot/ankle, a transitive benefit regarding energy use and conservation of such energy is provided. By assisting the tendons in generating force, less energy is being used to accomplish the same amount of work, thereby reducing the usage of energy generated while increasing the amount of available energy.

Although the present disclosure has been described with reference to exemplary embodiments and implementations thereof, the present disclosure is not limited by or to such exemplary embodiments/implementations. For example, it is contemplated that propulsion band(s) associated with the disclosed socks may be joined to the underlying sock structure/fabric in various ways. Thus, the propulsion band(s) may be embedded within the sock structure/fabric, in whole or in part, or may be adhered relative to the sock structure/fabric, in whole or in part. For example, the propulsion band(s) may be attached relative to the sock structure/fabric at distinct points (e.g., at the top of the sock, at the bottom of the sock and/or at one or more intermediate points along the sock). Different adherence techniques/mechanisms can be employed for non-embedded propulsion band(s), e.g., the propulsion band(s) may be stitched relative to the sock structure/fabric at discrete points along the sock. In addition, it is noted that propulsion band(s) that are adhered relative to the sock structure/fabric may be adjusted/adjustable, e.g., by the user, to tighten or loosen the propulsion band(s). In an exemplary embodiment, propulsion band(s) may be adhered relative to the sock structure/fabric by one or more VELCRO® closures, thereby facilitating propulsion band adjustment. The adjustment functionality may be effectuated by adjusting the propulsion band(s) adherence at the top of the sock, at the bottom of the sock and/or at one or more intermediate points along the length of the sock. Additional modifications and/or refinements to the disclosed propulsion socks may be undertaken without departing from the spirit and/or scope of the present disclosure.

Although the devices and methods of the present disclosure have been described with reference to exemplary embodiments thereof, the present disclosure is not limited to such exemplary embodiments and/or implementations. Rather, the devices and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

What is claimed is:
1. A dynamic sock, comprising:
a main body section configured to cover at least a portion of a foot and a lower leg of a user, the main body section fabricated from a material configured to impart a compressive force against the portion of the foot and the lower leg of the user;
a propulsion band fabricated from an elastic material and coupled to or integrated into the main body section to define a band path, the band path, when worn by the user, extending from a first section of the propulsion band superior to metatarsals heads of the foot, traversing medially and laterally of the metatarsal heads in a second section of the propulsion band, traversing inferiorly to an arch of the foot in a third section of the propulsion band, and extending posteriorly underneath a heel section of the dynamic sock in a fourth section of the propulsion band;
an elastic top cuff joined to a fifth section of the propulsion band and, when worn by the user, spaced from the heel section of the dynamic sock and configured to reduce slippage relative to the lower leg of the user;
wherein a distance measured from a bottom-most point of the heel section of the dynamic sock to the elastic top cuff is a sock height, wherein, in the fifth section, the propulsion band extends vertically from the fourth section of the propulsion band in the heel section of the dynamic sock up a majority of the sock height continuously within a back half portion of the dynamic sock and defining a rear-most extent of the dynamic sock; and wherein the propulsion band is adapted to load an elastic spring force during dorsiflexion based on tension generated between the fourth section and the elastic top cuff, and adapted to release the elastic spring force during plantarflexion, thereby increasing user propulsion at the plantarflexion.

2. The dynamic sock of claim 1, wherein the band path, when worn by the user, extends superiorly up a back of a calf in the fifth section of the propulsion band.

3. The dynamic sock of claim 2, wherein the band path splits into a substantially V-shaped section adapted to be disposed at or near an upper part of the calf of the user, when worn, in a sixth section of the propulsion band.

4. The dynamic sock of claim 3, wherein the band path, when worn, wraps around the lower leg medially and laterally, joining and terminating at a shin inferior to a patella of the user in a seventh section of the propulsion band.

5. The dynamic sock of claim 1, wherein a compression value of the propulsion band is greater than a compression value of the main body section.

6. The dynamic sock of claim 1, wherein a compression value of the main body section is 8 mmHg to 15 mmHg, inclusive, and a compression value of the propulsion band is 15 mmHg to 20 mmHg, inclusive.

7. The dynamic sock of claim 1, wherein the main body section is woven and the propulsion band is integrated into the main body section by stitching an elastic thread into the main body section along the band path.

8. The dynamic sock of claim 7, wherein the main body section includes a low compression or density weave and the propulsion band includes a high compression or density weave.

9. The dynamic sock of claim 1, wherein the propulsion band is integrated into the main body section by Jacquard knitting an elastic thread into the main body section at the band path.

10. The dynamic sock of claim 1, wherein the propulsion band defines an elongated elastic material coupled to an outer surface of the main body section along the band path.

11. The dynamic sock of claim 1, wherein the propulsion band is moveable relative to the main body section to allow for adjustment of the band path.

12. The dynamic sock of claim 1, wherein the propulsion band is moveable relative to the main body section to allow for an increase or decrease in tension provided by the propulsion band.

13. The dynamic sock of claim 1, wherein the main body section includes a pocket formed at or near a shin area of the dynamic sock, the pocket configured to removably receive a shin guard.

14. The dynamic sock of claim 1, wherein the main body section is fabricated from spandex.

15. The dynamic sock of claim 1, wherein the propulsion band is fabricated from a material including 70-90% polyester and 10-30% rubber.

16. A method of providing plantarflexion propulsion to a user, the method comprising:
providing a dynamic sock and donning the dynamic sock onto the user, the dynamic sock including a main body section, a propulsion band fabricated from an elastic material and coupled to or integrated into the main body section to define a band path, and an elastic top cuff, wherein (i) the main body section covering at least a portion of a foot and a lower leg of the user, (ii) the band path extending from a first section of the propulsion band superior to metatarsals heads of the foot, traversing medially and laterally of the metatarsal heads in a second section of the propulsion band, traversing inferiorly to an arch of the foot in a third section of the propulsion band, and extending posteriorly underneath a heel section of the dynamic sock in a fourth section of the propulsion band, and (iii) an elastic top cuff joined to a fifth section of the propulsion band, the elastic top cuff being spaced from the heel section of the dynamic sock and reducing slippage relative to the lower leg of the user, wherein a distance measured from a bottom-most point of the heel section of the dynamic sock to the elastic top cuff is a sock height, wherein, in the fifth section, the propulsion band extends vertically from the fourth section of the propulsion band in the heel section of the dynamic sock up a majority of the sock height continuously within a back half portion of the dynamic sock and defining a rear-most extent of the dynamic sock;
imparting a compressive force against the portion of the foot and the lower leg of the user with the main body section; and
increasing propulsion at plantarflexion with the propulsion band by loading an elastic spring force during dorsiflexion based on tension generated between the fourth section and the elastic top cuff and then releasing the elastic spring force during the plantarflexion.

\* \* \* \* \*